(12) United States Patent
Yamasaki et al.

(10) Patent No.: US 9,150,931 B2
(45) Date of Patent: Oct. 6, 2015

(54) FOOD-POISONING BACTERIA DETECTION CARRIER, AND METHOD FOR DETECTING FOOD-POISONING BACTERIA

(75) Inventors: Takaaki Yamasaki, Yokohama (JP); Takaaki Harada, Yokohama (JP); Yoshihiro Saruwatari, Yokohama (JP); Shuichi Kamei, Kudamatsu (JP)

(73) Assignees: TOYO SEIKAN GROUP HOLDINGS, LTD., Tokyo (JP); Toyo Kohan Co., Ltd., Tokyo (JP)

( * ) Notice: Subject to any disclaimer, the term of this patent is extended or adjusted under 35 U.S.C. 154(b) by 79 days.

(21) Appl. No.: 13/696,196

(22) PCT Filed: May 10, 2011

(86) PCT No.: PCT/JP2011/002592
§ 371 (c)(1),
(2), (4) Date: Nov. 5, 2012

(87) PCT Pub. No.: WO2011/142119
PCT Pub. Date: Nov. 17, 2011

(65) Prior Publication Data
US 2013/0143759 A1    Jun. 6, 2013

(30) Foreign Application Priority Data
May 12, 2010 (JP) .................... 2010-110293

(51) Int. Cl.
C12M 1/34        (2006.01)
C07H 21/04       (2006.01)
C12Q 1/68        (2006.01)

(52) U.S. Cl.
CPC .................. C12Q 1/689 (2013.01)

(58) Field of Classification Search
None
See application file for complete search history.

(56) References Cited

U.S. PATENT DOCUMENTS

| | | | |
|---|---|---|---|
| 2001/0053519 A1* | 12/2001 | Fodor et al. ................ 435/6 |
| 2010/0075305 A1 | 3/2010 | Ezaki et al. | |
| 2013/0059756 A1 | 3/2013 | Yamasaki et al. | |

FOREIGN PATENT DOCUMENTS

| CN | 101558168 A | 10/2009 |
|---|---|---|
| JP | 2005-034121 A | 2/2005 |
| JP | 2006-166912 A | 6/2006 |
| JP | 2008-200012 A | 9/2008 |
| KR | 2009-0027875 A | 3/2009 |
| WO | WO 2008/041354 A1 | 4/2008 |

OTHER PUBLICATIONS

Wang et al. Appl Microbiol Biotechnol 2007 vol. 76 pp. 225-233.*
PCT, "International Search Report and Written Opinion for PCT/JP2011/002592", Jul. 19, 2011.
Thompson FL., et al., "Phylogeny and molecular identification of vibrios on the basis of multilocus sequence analysis", Applied and Environmental Microbiology, Sep. 2005, vol. 71.
European Patent Office, "Extended European Search Report for EP 11780378.3", Sep. 6, 2013.
Suo B. et al., "Development of an oligonucleotide-based microarray to detect . . . ", Molecular and Cellular Probes, Academic Press, London GB, vol. 24, No. 2, Apr. 1, 2010, p. 77-86.
Lim Miao Chu et al., "Use of oligonucleotide array for . . . ", Journal of Food Protection, Int'l Assn for Food Protection, US, vol. 68, No. 11, Nov. 1, 2005, p. 2278-2286.
S.-Q. Jin et al., "Multiplexed Bead-Based Mesofluidic System for Detection of . . . ", Applied and Environmental Microbiology, vol. 75, No. 21, Nov. 1, 2009, p. 6647-6654.
Yiwen Liu-Stratton et al., "DNA Microarray technology in nutraceutical and food safety", Toxicology Letters, vol. 150, No. 1, Apr. 1, 2004, p. 29-42.
Fukushima, Hiroshi, "Simultaneous Multiplex Real-time SYBR Green PCR Analysis of 24 Target Genes of Food-Borne Bacteria"; Shimane Prefectural Institute of Public Health and Environment Science Ho, No. 50; Dec. 28, 2009; pp. 41-51.
China Patent Office, "Office Action for 201180018595.8," Oct. 31, 2013.
Bang-Xing Hong et al., "Application of oligonucleotide array technology in rapid detection of common bacteria of foodborne diseases," Chinese Journal of Laboratory Medicine, Feb. 2005, p. 169-172, vol. 28, No. 2, Department of Microbiology, School of Medicine, Sun Yatsen University, Guangzhou 510089, China.

* cited by examiner

*Primary Examiner* — Amanda Haney
(74) *Attorney, Agent, or Firm* — Osha Liang LLP

(57) ABSTRACT

A plurality of probes are immobilized on a carrier for detecting food poisoning bacteria, the plurality of probes being selected, either alone or in combination, respectively from two or more groups among a first probe group for detecting *Escherichia coli*, a second probe group for detecting *Listeria*, a third probe group for detecting *Campylobacter*, a fourth probe group for detecting *Vibrio parahaemolyticus*, a fifth probe group for detecting *Staphylococcus aureus*, a sixth probe group for detecting *Salmonella*, and a seventh probe group for detecting *Bacillus cereus*. Two or more types of food poisoning bacteria among *Escherichia coli*, *Listeria*, *Campylobacter*, *Vibrio parahaemolyticus*, *Staphylococcus aureus*, *Salmonella*, and *Bacillus cereus* can be specifically and simultaneously detected using the carrier.

2 Claims, 16 Drawing Sheets

FIG. 1

| DETECTION TARGET FOOD POISONING BACTERIA | TARGET REGION | PROBE | |
|---|---|---|---|
| | | SEQ ID NO. | BASE SEQUENCE |
| Escherichia coli | dnaJ (HEAT SHOCK PROTEIN GENE) | 1 | GGTAAAGGCGTCAAGTCTGTC |
| | | 2 | GCGGTGCTGATTACGCTATAAC |
| | | 3 | ATTTACGCTATAACATGGAGCTCA |
| | | 4 | ATTTACGCTATAACATGGAGCTCACC |
| | pyrH (URIDINE MONOPHOSPHATE KINASE GENE) | 5 | AGAAGCTATCAGCCTGTTGCGC |
| | | 6 | GCGCAACAGGCTGATAGCTTCT |
| Listeria spp. | dnaJ (HEAT SHOCK PROTEIN GENE) | 7 | CTTGGTTTGGATCTACGTGTCCATAT |
| | | 8 | CGTGTCCATATTGATCATATTGCG |
| | | 9 | TGATCATATTGCGCACGTTTTT |
| | | 10 | ATATTGCGCACGTTTTTGTGG |
| | | 11 | GTTTTTGTGGGTCACTTAATGCTTC |
| | | 12 | CTTAATGCTTCATATGCCTCTGATATTTC |
| | | 13 | GCCTCTGATATTTCTTTAAATTTTTCATCA |
| | | 14 | GCCTCTCCCTCACTCTAGACTATCAGTTT |
| Campylobacter spp. | 16S rRNA (RIBOSOMAL GENE) | 15 | GGTGATATCTACGGATTTTACCCTA |
| | | 16 | CCTTCGCAATGGTATTCTTGG |
| | | 17 | AATGGGTATTCTTGGTGATATCTACGG |
| | | 18 | GGAACTCAACTGACGCTAAGGC |
| | | 19 | ACTCAACTGACGCTAAGGCG |
| Vibrio parahaemolyticus | tdh (THERMOSTABLE DIRECT HEMOLYSIN GENE) | 20 | CCGTAATGTAAAAGAAAACCGTACA |
| | | 21 | GTAATGTAAAAGAAAACCGTACAAAGATG |
| | | 22 | GAAAACCGTACAAAGATGTTTATGGTC |
| | | 23 | GTTTATGGTCAATCAGTATTCACAACG |
| | | 24 | AATCAGTATTCACAACGTCAGGTACTAAA |

FIG.2

| DETECTION TARGET FOOD POISONING BACTERIA | TARGET REGION | PROBE | |
|---|---|---|---|
| | | SEQ ID NO. | BASE SEQUENCE |
| Staphylococcus aureus | dnaJ (HEAT SHOCK PROTEIN GENE) | 25 | CAAGCTTCTTCAAATTCTTGACCAC |
| | | 26 | ACTTCCATTACATTTAGGACAAACTTGTTC |
| | | 27 | CTTCTTCAAATTCTTGACCACTTCC |
| | | 28 | CAAACTTGTTCAGTACGAACTCTACCTAA |
| | | 29 | CGAACTCTACCTAAAATTGTGTTTGTTC |
| | | 30 | CCACTGCCGGTTTTGTTATTT |
| | | 31 | CCGGTTTTGTTATTTTATCGGTG |
| | | 32 | GGTGGTTTTAAGCGTACTCTTCTATTTTAA |
| | | 33 | GTTTTAAGCGTACTCTTCTATTTTAAATTCC |
| | | 34 | TCTATTTTAAATTCCGTGAAGCAAAAC |
| Salmonella spp. | invA (INVASION GENE) | 35 | TTTAAATTCCGTGAAGCAAAACGT |
| | | 36 | CAAGTTGAGCTTTTTCCAGATCTTCA |
| | | 37 | CTCTTCGGCACAAGTAATATCAACG |
| | | 38 | GGCACAAGTAATATCAACGGTACG |
| | | 39 | GCTCTTCGGCACAAGTAATATCAA |
| | | 40 | AGCTTTTTCCAGATCTTCACGC |
| Bacillus cereus | nhe (NON-HEMOLYTIC ENTEROTOXIN GENE) | 41 | GCTTATTTCAACGAATCAAATATCATTAC |
| | | 42 | ATTTCAACGAATCAAATATCATTATTACTACA |
| | | 43 | CAAAATATCATTAACTACTACAATACGAAATTCC |
| | | 44 | CGAAATTCCAAAACTATTATGATACTTTAGTTG |
| | | 45 | AAAACTATTATGATACTTTAGTTGCTGCTG |
| | cesB (CEREULIDE SYNTHETASE GENE) | 46 | GAGAAATATGAAATTCTAGAGATGAACAAT |
| | | 47 | GAAATTCTAGAGATGAACAATAATTCAACG |
| | | 48 | TTATGGAAGAAACAAAAGGACTGAGA |
| | | 49 | GAAGAAACAAAAGGACTGAGAAGGA |

FIG. 3

| AMPLIFICATION TARGET FOOD POISONING BACTERIA | TARGET REGION | AMPLIFIED PRODUCT | PRIMER | | |
|---|---|---|---|---|---|
| | | | SEQ ID NO. | F/R | BASE SEQUENCE |
| Escherichia coli | pyrH | 157 | 50 | F | CGCTCGTCTGATGTCCGCTATTCCATTGAAT |
| | | | 51 | R | ACCACGCAGGCAAGCTGCTGAGTCGG |
| Listeria spp. | dnaJ | 176 | 52 | F | CTTCAAATCCAGAGAATCCTCCACCGC |
| | | | 53 | R | GAGAATCCTCCACCGCTAAATCCGCC |
| Campylobacter spp. | 16S rRNA | 263 | 54 | F | GGTGATATCTACGGATTTTACCCCTA |
| | | | 55 | R | AATGGGTATTCTTGGTGATATCTACGG |
| Vibrio parahaemolyticus | tdh | 380 | 56 | F | TCAGTTTACTTTTTTGGGTTTTTTGGCTTTCATGAAAACCTG |
| | | | 57 | R | TCATTAATGTTCACAGTCATGTAGGATGTCAGCC |
| Staphylococcus aureus | dnaJ | 236 | 58 | F | CACGCCTGGAGAGCCTTCACCAGC |
| | | | 59 | R | GTTACTGTAATGGCCGTCATGTAGCTG |
| Salmonella spp. | invA | 180 | 60 | F | GAACAACCCATTGTATTGGTTGTTACGGC |
| | | | 61 | R | GGCTGCTCGCCTTTGCTGGTTTT |
| Bacillus cereus | nhe | 195 | 62 | F | CATCTGTTGATGCGGCTTTAAAAGGGAAGT |
| | | | 63 | R | GAGTCGCTTTATCCTTTGCATCTACCGCAG |
| | cesB | 238 | 64 | F | CACCTGCCGGAGGAGCAAAATGATACAAC |
| | | | 65 | R | CAGATTCATTCTTCGCTTATGGTGGTGACTC |

FIG. 7

| | Escherichia coli | | Listeria spp. | | Campylobacter spp. | | Vibrio parahaemolyticus |
|---|---|---|---|---|---|---|---|
| 1 | 168 | 7 | 552 | 14 | 16320 | 20 | 19033 |
| 2 | 11750 | 8 | 130 | 15 | 3532 | 21 | 21788 |
| 3 | 13049 | 9 | 758 | 16 | 860 | 22 | 18097 |
| 4 | 16583 | 10 | 1891 | 17 | 2324 | 23 | 16001 |
| 5 | 168 | 11 | 8687 | 18 | 4477 | 24 | 11982 |
| 6 | 2091 | 12 | 11211 | 19 | 2755 | – | – |
| – | – | 13 | 10108 | – | – | – | – |

| | Staphylococcus aureus | | Salmonella spp. | | Bacillus cereus nhe | | Bacillus cereus cesB |
|---|---|---|---|---|---|---|---|
| 25 | 7718 | 30 | 1901 | 41 | 2648 | 46 | 252 |
| 26 | 9788 | 31 | 1820 | 42 | 4304 | 47 | 253 |
| 27 | 10827 | 32 | 3658 | 43 | 10824 | 48 | 26610 |
| 28 | 15628 | 33 | 8349 | 44 | 9516 | 49 | 19022 |
| 29 | 15876 | 34 | 14665 | 45 | 3455 | – | – |
| – | – | 35 | 13398 | – | – | – | – |
| – | – | 36 | 173 | – | – | – | – |
| – | – | 37 | 190 | – | – | – | – |
| – | – | 38 | 188 | – | – | – | – |
| – | – | 39 | 193 | – | – | – | – |
| – | – | 40 | 190 | – | – | – | – |

FIG. 11

| SEQ ID NO. | DETECTION TARGET FOOD POISONING BACTERIA/TARGET REGION | FLUORESCENCE INTENSITY |
|---|---|---|
| 1 | Escherichia coli dnaJ | 0 |
| 2 | | 0 |
| 3 | | 0 |
| 4 | | 0 |
| 5 | Escherichia coli pyrH | 129 |
| 6 | | 12466 |
| 7 | | 634 |
| 8 | | 142 |
| 9 | Listeria dnaJ | 1443 |
| 10 | | 3509 |
| 11 | | 12494 |
| 12 | | 18391 |
| 13 | | 23972 |
| 14 | Campylobacter 16S rRNA | 57855 |
| 15 | | 18616 |
| 16 | | 4363 |
| 17 | | 14116 |
| 18 | | 2708 |
| 19 | | 1416 |
| 20 | Vibrio parahaemolyticus tdh | 23811 |
| 21 | | 36082 |
| 22 | | 46894 |
| 23 | | 37823 |
| 24 | | 32691 |

| SEQ ID NO. | DETECTION TARGET FOOD POISONING BACTERIA/TARGET REGION | FLUORESCENCE INTENSITY |
|---|---|---|
| 25 | Staphylococcus aureus dnaJ | 30034 |
| 26 | | 61417 |
| 27 | | 47041 |
| 28 | | 63359 |
| 29 | | 64121 |
| 30 | | 12178 |
| 31 | | 25133 |
| 32 | | 44506 |
| 33 | | 62919 |
| 34 | Salmonella invA | 63320 |
| 35 | | 62446 |
| 36 | | 429 |
| 37 | | 349 |
| 38 | | 209 |
| 39 | | 222 |
| 40 | | 159 |
| 41 | Bacillus cereus nhe | 2287 |
| 42 | | 3454 |
| 43 | | 8045 |
| 44 | | 13195 |
| 45 | | 18363 |
| 46 | Bacillus cereus cesB | 94 |
| 47 | | 78 |
| 48 | | 24679 |
| 49 | | 23562 |

FIG. 12

| PROBE | DNA SAMPLE | | | | | | | |
|---|---|---|---|---|---|---|---|---|
| | Escherichia coli pyrH | Listeria | Campylobacter | Vibrio parahaemolyticus | Staphylococcus aureus | Salmonella | Bacillus cereus nhe | Bacillus cereus cesB | A PLURALITY OF DNA |
| PROBE FOR DETECTING pyrH OF Escherichia coli | + | − | − | − | − | − | − | − | + |
| PROBE FOR DETECTING Listeria | − | + | − | − | − | − | − | − | + |
| PROBE FOR DETECTING Campylobacter | − | − | + | − | − | − | − | − | + |
| PROBE FOR DETECTING Vibrio parahaemolyticus | − | − | − | + | − | − | − | − | + |
| PROBE FOR DETECTING Staphylococcus aureus | − | − | − | − | + | − | − | − | + |
| PROBE FOR DETECTING Salmonella | − | − | − | − | − | + | − | − | + |
| PROBE FOR DETECTING nhe of Bacillus cereus | − | − | − | − | − | − | + | − | + |
| PROBE FOR DETECTING cesB of Bacillus cereus | − | − | − | − | − | − | − | + | + |

| | PRESENCE OR ABSENCE OF DNA (○: PRESENT, ×: ABSENT) | | |
|---|---|---|---|
| | 5 | 6 | 7 |
| Escherichia coli | ○ | ○ | ○ |
| Listeria | ○ | ○ | ○ |
| Campylobacter | ○ | ○ | ○ |
| Vibrio parahaemolyticus | × | ○ | ○ |
| Staphylococcus aureus | ○ | × | ○ |
| Salmonella | ○ | ○ | ○ |
| Bacillus cereus | | | × |
| PROBE SPECIFICITY | ○ | ○ | ○ |
| CHIP RESULTS | | | |

FIG. 15

| SEQ ID NO. | DETECTION TARGET FOOD POISONING BACTERIA/TARGET REGION | FLUORESCENCE INTENSITY | | | |
|---|---|---|---|---|---|
| | | CHIP RESULTS 1 | CHIP RESULTS 2 | CHIP RESULTS 3 | CHIP RESULTS 4 |
| 1 | Escherichia coli dnaJ | 0 | 0 | 0 | 0 |
| 2 | | 0 | 0 | 0 | 0 |
| 3 | | 0 | 0 | 0 | 0 |
| 4 | | 0 | 0 | 0 | 0 |
| 5 | Escherichia coli pyrH | 122 | 14 | 0 | 57 |
| 6 | | 12493 | 873 | 0 | 13953 |
| 7 | Listeria dnaJ | 493 | 21 | 942 | 0 |
| 8 | | 124 | 14 | 277 | 0 |
| 9 | | 1553 | 58 | 2046 | 0 |
| 10 | | 3814 | 59 | 4802 | 0 |
| 11 | | 14405 | 327 | 19259 | 0 |
| 12 | | 21836 | 689 | 30665 | 0 |
| 13 | | 27681 | 939 | 40076 | 0 |
| 14 | Campylobacter 16S rRNA | 58521 | 0 | 60257 | 46791 |
| 15 | | 20567 | 0 | 19325 | 15969 |
| 16 | | 4907 | 0 | 5223 | 3673 |
| 17 | | 15449 | 0 | 12482 | 9475 |
| 18 | | 2858 | 0 | 3205 | 1824 |
| 19 | | 1782 | 0 | 2136 | 1137 |
| 20 | Vibrio parahaemolyticus tdh | 29670 | 1413 | 43198 | 17105 |
| 21 | | 42120 | 1369 | 56406 | 20445 |
| 22 | | 48342 | 1243 | 61321 | 33314 |
| 23 | | 46867 | 2165 | 59430 | 30492 |
| 24 | | 37270 | 1610 | 50886 | 23593 |
| 25 | Staphylococcus aureus dnaJ | 31948 | 2253 | 34743 | 28907 |
| 26 | | 60207 | 1049 | 58089 | 54378 |
| 27 | | 48674 | 1939 | 50625 | 40664 |
| 28 | | 63212 | 497 | 62360 | 63084 |
| 29 | | 63815 | 329 | 63442 | 64016 |
| 30 | Salmonella invA | 14496 | 814 | 15475 | 11504 |
| 31 | | 25747 | 1102 | 28582 | 23658 |
| 32 | | 44811 | 2708 | 44540 | 47844 |
| 33 | | 62130 | 813 | 59489 | 61230 |
| 34 | | 63121 | 647 | 62266 | 63177 |
| 35 | | 62485 | 1224 | 58478 | 62192 |
| 36 | | 340 | 17 | 409 | 335 |
| 37 | | 280 | 31 | 365 | 267 |
| 38 | | 190 | 22 | 232 | 164 |
| 39 | | 204 | 21 | 274 | 174 |
| 40 | | 137 | 26 | 213 | 147 |
| 41 | Bacillus cereus nhe | 0 | 125 | 4503 | 1078 |
| 42 | | 0 | 179 | 6502 | 1598 |
| 43 | | 0 | 505 | 15990 | 3681 |
| 44 | | 0 | 435 | 24224 | 5862 |
| 45 | | 0 | 542 | 34161 | 8690 |
| 46 | Bacillus cereus cesB | 0 | 14 | 136 | 68 |
| 47 | | 0 | 17 | 129 | 68 |
| 48 | | 0 | 1043 | 48054 | 19931 |
| 49 | | 0 | 2262 | 47613 | 20895 |

FIG. 16

| SEQ ID NO. | DETECTION TARGET FOOD POISONING BACTERIA/ TARGET REGION | FLUORESCENCE INTENSITY | | |
|---|---|---|---|---|
| | | CHIP RESULTS 5 | CHIP RESULTS 6 | CHIP RESULTS 7 |
| 1 | Escherichia coli dnaJ | 0 | 0 | 0 |
| 2 | | 0 | 0 | 0 |
| 3 | | 0 | 0 | 0 |
| 4 | | 0 | 0 | 0 |
| 5 | Escherichia coli pyrH | 71 | 86 | 92 |
| 6 | | 11452 | 9996 | 10994 |
| 7 | | 552 | 418 | 415 |
| 8 | | 139 | 129 | 90 |
| 9 | Listeria dnaJ | 1395 | 1004 | 894 |
| 10 | | 3285 | 2105 | 2066 |
| 11 | | 11367 | 9073 | 9138 |
| 12 | | 16049 | 14350 | 14002 |
| 13 | | 20829 | 18874 | 19940 |
| 14 | | 48204 | 49887 | 53750 |
| 15 | | 16309 | 16061 | 16238 |
| 16 | Campylobacter 16S rRNA | 3709 | 3312 | 3329 |
| 17 | | 11676 | 10190 | 10312 |
| 18 | | 2287 | 1997 | 2097 |
| 19 | | 1441 | 1093 | 1317 |
| 20 | Vibrio parahaemolyticus tdh | 23944 | 26284 | 0 |
| 21 | | 33717 | 34467 | 0 |
| 22 | | 45314 | 43293 | 0 |
| 23 | | 39151 | 38534 | 0 |
| 24 | | 31342 | 29475 | 0 |
| 25 | Staphylococcus aureus dnaJ | 36013 | 0 | 29407 |
| 26 | | 61757 | 0 | 56085 |
| 27 | | 44968 | 0 | 40390 |
| 28 | | 63317 | 0 | 62191 |
| 29 | | 64091 | 0 | 63559 |
| 30 | Salmonella invA | 0 | 12343 | 13750 |
| 31 | | 0 | 25448 | 26712 |
| 32 | | 0 | 47587 | 48393 |
| 33 | | 0 | 61752 | 62197 |
| 34 | | 0 | 62874 | 62980 |
| 35 | | 0 | 62698 | 62531 |
| 36 | | 0 | 167 | 337 |
| 37 | | 0 | 104 | 279 |
| 38 | | 0 | 74 | 163 |
| 39 | | 0 | 126 | 159 |
| 40 | | 0 | 98 | 239 |
| 41 | Bacillus cereus nhe | 2057 | 2070 | 2132 |
| 42 | | 2866 | 3023 | 3244 |
| 43 | | 6683 | 7117 | 7686 |
| 44 | | 9206 | 10732 | 11723 |
| 45 | | 13826 | 14645 | 19050 |
| 46 | Bacillus cereus cesB | 60 | 62 | 88 |
| 47 | | 72 | 64 | 82 |
| 48 | | 26817 | 22407 | 27531 |
| 49 | | 29606 | 21582 | 25169 |

SEQUENCE LISTING

```
<160> NUMBER OF SEQ ID NOS: 67

<210> SEQ ID NO 1
<211> LENGTH: 21
<212> TYPE: DNA
<213> ORGANISM: Escherichia coli

<400> SEQUENCE: 1
ggtaaaggcg tcaagtctgt c                                         21

<210> SEQ ID NO 2
<211> LENGTH: 23
<212> TYPE: DNA
<213> ORGANISM: Escherichia coli

<400> SEQUENCE: 2
gcggtgctga tttacgctat aac                                       23

<210> SEQ ID NO 3
<211> LENGTH: 24
<212> TYPE: DNA
<213> ORGANISM: Escherichia coli

<400> SEQUENCE: 3
atttacgcta taacatggag ctca                                      24
```

<210> SEQ ID NO 4
<211> LENGTH: 26
<212> TYPE: DNA
<213> ORGANISM: Escherichia coli

<400> SEQUENCE: 4
atttacgcta taacatggag ctcacc                                          26

<210> SEQ ID NO 5
<211> LENGTH: 22
<212> TYPE: DNA
<213> ORGANISM: Escherichia coli

<400> SEQUENCE: 5
agaagctatc agcctgttgc gc                                              22

<210> SEQ ID NO 6
<211> LENGTH: 22
<212> TYPE: DNA
<213> ORGANISM: Escherichia coli

<400> SEQUENCE: 6
gcgcaacagg ctgatagctt ct                                              22

<210> SEQ ID NO 7
<211> LENGTH: 26
<212> TYPE: DNA
<213> ORGANISM: Listeria

<400> SEQUENCE: 7
cttggtttgg atctacgtgt ccatat                                          26

<210> SEQ ID NO 8
<211> LENGTH: 24
<212> TYPE: DNA
<213> ORGANISM: Listeria

<400> SEQUENCE: 8
cgtgtccata ttgatcatat tgcg                                            24

<210> SEQ ID NO 9
<211> LENGTH: 22
<212> TYPE: DNA
<213> ORGANISM: Listeria

<400> SEQUENCE: 9
tgatcatatt gcgcacgttt tt                                              22

<210> SEQ ID NO 10
<211> LENGTH: 21
<212> TYPE: DNA
<213> ORGANISM: Listeria

<400> SEQUENCE: 10
atattgcgca cgttttttgtg g                                              21

<210> SEQ ID NO 11
<211> LENGTH: 25
<212> TYPE: DNA
<213> ORGANISM: Listeria

<400> SEQUENCE: 11

-continued gtttttgtgg gtcacttaat gcttc                                          25

<210> SEQ ID NO 12
<211> LENGTH: 29
<212> TYPE: DNA
<213> ORGANISM: Listeria

<400> SEQUENCE: 12
cttaatgctt catatgcctc tgatatttc                                      29

<210> SEQ ID NO 13
<211> LENGTH: 30
<212> TYPE: DNA
<213> ORGANISM: Listeria

<400> SEQUENCE: 13
gcctctgata tttctttaaa tttttcatca                                     30

<210> SEQ ID NO 14
<211> LENGTH: 29
<212> TYPE: DNA
<213> ORGANISM: Campylobacter

<400> SEQUENCE: 14
gcctctccct cactctagac tatcagttt                                      29

<210> SEQ ID NO 15
<211> LENGTH: 26
<212> TYPE: DNA
<213> ORGANISM: Campylobacter

<400> SEQUENCE: 15
ggtgatatct acggatttta ccccta                                         26

<210> SEQ ID NO 16
<211> LENGTH: 22
<212> TYPE: DNA
<213> ORGANISM: Campylobacter

<400> SEQUENCE: 16
ccttcgcaat gggtattctt gg                                             22

<210> SEQ ID NO 17
<211> LENGTH: 27
<212> TYPE: DNA
<213> ORGANISM: Campylobacter

<400> SEQUENCE: 17
aatgggtatt cttggtgata tctacgg                                        27

<210> SEQ ID NO 18
<211> LENGTH: 22
<212> TYPE: DNA
<213> ORGANISM: Campylobacter

<400> SEQUENCE: 18
ggaactcaac tgacgctaag gc                                             22

<210> SEQ ID NO 19
<211> LENGTH: 20
<212> TYPE: DNA
<213> ORGANISM: Campylobacter

<400> SEQUENCE: 19

```
actcaactga cgctaaggcg                                              20
```

<210> SEQ ID NO 20
<211> LENGTH: 26
<212> TYPE: DNA
<213> ORGANISM: Vibrio parahaemolyticus

<400> SEQUENCE: 20

```
ccgtaatgta aaagaaaac cgtaca                                        26
```

<210> SEQ ID NO 21
<211> LENGTH: 30
<212> TYPE: DNA
<213> ORGANISM: Vibrio parahaemolyticus

<400> SEQUENCE: 21

```
gtaatgtaaa aagaaaaccg tacaaagatg                                   30
```

<210> SEQ ID NO 22
<211> LENGTH: 27
<212> TYPE: DNA
<213> ORGANISM: Vibrio parahaemolyticus

<400> SEQUENCE: 22

```
gaaaaccgta caaagatgtt tatggtc                                      27
```

<210> SEQ ID NO 23
<211> LENGTH: 27
<212> TYPE: DNA
<213> ORGANISM: Vibrio parahaemolyticus

<400> SEQUENCE: 23

```
gtttatggtc aatcagtatt cacaacg                                      27
```

<210> SEQ ID NO 24
<211> LENGTH: 29
<212> TYPE: DNA
<213> ORGANISM: Vibrio parahaemolyticus

<400> SEQUENCE: 24

```
aatcagtatt cacaacgtca ggtactaaa                                    29
```

<210> SEQ ID NO 25
<211> LENGTH: 25
<212> TYPE: DNA
<213> ORGANISM: Staphylococcus aureus

<400> SEQUENCE: 25

```
caagcttctt caaattcttg accac                                        25
```

<210> SEQ ID NO 26
<211> LENGTH: 30
<212> TYPE: DNA
<213> ORGANISM: Staphylococcus aureus

<400> SEQUENCE: 26

```
acttccatta catttaggac aaacttgttc                                   30
```

<210> SEQ ID NO 27
<211> LENGTH: 25
<212> TYPE: DNA
<213> ORGANISM: Staphylococcus aureus -continued

```
<400> SEQUENCE: 27
cttcttcaaa ttcttgacca cttcc                                          25

<210> SEQ ID NO 28
<211> LENGTH: 29
<212> TYPE: DNA
<213> ORGANISM: Staphylococcus aureus

<400> SEQUENCE: 28
caaacttgtt cagtacgaac tctacctaa                                      29

<210> SEQ ID NO 29
<211> LENGTH: 29
<212> TYPE: DNA
<213> ORGANISM: Staphylococcus aureus

<400> SEQUENCE: 29
cgaactctac ctaaaattgt gttttgttc                                      29

<210> SEQ ID NO 30
<211> LENGTH: 23
<212> TYPE: DNA
<213> ORGANISM: Salmonella enterica

<400> SEQUENCE: 30
ccactgccgg tttttgttat ttt                                            23

<210> SEQ ID NO 31
<211> LENGTH: 24
<212> TYPE: DNA
<213> ORGANISM: Salmonella enterica

<400> SEQUENCE: 31
ccggtttttg ttattttatc ggtg                                           24

<210> SEQ ID NO 32
<211> LENGTH: 30
<212> TYPE: DNA
<213> ORGANISM: Salmonella enterica

<400> SEQUENCE: 32
ggtggtttta agcgtactct tctatttaa                                      30

<210> SEQ ID NO 33
<211> LENGTH: 31
<212> TYPE: DNA
<213> ORGANISM: Salmonella enterica

<400> SEQUENCE: 33
gttttaagcg tactcttcta ttttaaattc c                                   31

<210> SEQ ID NO 34
<211> LENGTH: 27
<212> TYPE: DNA
<213> ORGANISM: Salmonella enterica

<400> SEQUENCE: 34
tctattttaa attccgtgaa gcaaaac                                        27

<210> SEQ ID NO 35
<211> LENGTH: 24
<212> TYPE: DNA
<213> ORGANISM: Salmonella enterica
```

-continued

```
<400> SEQUENCE: 35
tttaaattcc gtgaagcaaa acgt                                          24

<210> SEQ ID NO 36
<211> LENGTH: 26
<212> TYPE: DNA
<213> ORGANISM: Salmonella enterica

<400> SEQUENCE: 36
caagttgagc tttttccaga tcttca                                        26

<210> SEQ ID NO 37
<211> LENGTH: 25
<212> TYPE: DNA
<213> ORGANISM: Salmonella enterica

<400> SEQUENCE: 37
ctcttcggca caagtaatat caacg                                         25

<210> SEQ ID NO 38
<211> LENGTH: 24
<212> TYPE: DNA
<213> ORGANISM: Salmonella enterica

<400> SEQUENCE: 38
ggcacaagta atatcaacgg tacg                                          24

<210> SEQ ID NO 39
<211> LENGTH: 24
<212> TYPE: DNA
<213> ORGANISM: Salmonella enterica

<400> SEQUENCE: 39
gctcttcggc acaagtaata tcaa                                          24

<210> SEQ ID NO 40
<211> LENGTH: 22
<212> TYPE: DNA
<213> ORGANISM: Salmonella enterica

<400> SEQUENCE: 40 agcttttttcc agatcttcac gc                                           22

<210> SEQ ID NO 41
<211> LENGTH: 29
<212> TYPE: DNA
<213> ORGANISM: Bacillus cereus

<400> SEQUENCE: 41
gcttatttca acgaatcaaa tatcattac                                     29

<210> SEQ ID NO 42
<211> LENGTH: 30
<212> TYPE: DNA
<213> ORGANISM: Bacillus cereus

<400> SEQUENCE: 42
atttcaacga atcaaaatat cattactaca                                    30

<210> SEQ ID NO 43
<211> LENGTH: 31
<212> TYPE: DNA
```

<213> ORGANISM: Bacillus cereus

<400> SEQUENCE: 43
caaaatatca ttaactacaa tacgaaattc c 31

<210> SEQ ID NO 44
<211> LENGTH: 33
<212> TYPE: DNA
<213> ORGANISM: Bacillus cereus

<400> SEQUENCE: 44
cgaaattcca aaactattat gatactttag ttg 33

<210> SEQ ID NO 45
<211> LENGTH: 30
<212> TYPE: DNA
<213> ORGANISM: Bacillus cereus

<400> SEQUENCE: 45
aaaactatta tgatacttta gttgctgctg 30

<210> SEQ ID NO 46
<211> LENGTH: 30
<212> TYPE: DNA
<213> ORGANISM: Bacillus cereus

<400> SEQUENCE: 46
gagaaatatg aaattctaga gatgaacaat 30

<210> SEQ ID NO 47
<211> LENGTH: 30
<212> TYPE: DNA
<213> ORGANISM: Bacillus cereus

<400> SEQUENCE: 47
gaaattctag agatgaacaa taattcaacg 30

<210> SEQ ID NO 48
<211> LENGTH: 27
<212> TYPE: DNA
<213> ORGANISM: Bacillus cereus

<400> SEQUENCE: 48
ttatggaaga aacaaaaagg actgaga 27

<210> SEQ ID NO 49
<211> LENGTH: 26
<212> TYPE: DNA
<213> ORGANISM: Bacillus cereus

<400> SEQUENCE: 49
gaagaaacaa aaaggactga gaagga 26

<210> SEQ ID NO 50
<211> LENGTH: 31
<212> TYPE: DNA
<213> ORGANISM: Escherichia coli

<400> SEQUENCE: 50
cgctcgtctg atgtccgcta ttccattgaa t 31

<210> SEQ ID NO 51
<211> LENGTH: 26

```
<212> TYPE: DNA
<213> ORGANISM: Escherichia coli

<400> SEQUENCE: 51
accacgcagg caagctgctg agtcgg                                         26

<210> SEQ ID NO 52
<211> LENGTH: 27
<212> TYPE: DNA
<213> ORGANISM: Listeria monocytogenes

<400> SEQUENCE: 52
cttcaaatcc agagaatcct ccaccgc                                        27

<210> SEQ ID NO 53
<211> LENGTH: 26
<212> TYPE: DNA
<213> ORGANISM: Listeria monocytogenes

<400> SEQUENCE: 53
gagaatcctc caccgctaaa tccgcc                                         26

<210> SEQ ID NO 54
<211> LENGTH: 26
<212> TYPE: DNA
<213> ORGANISM: Campylobacter jejuni

<400> SEQUENCE: 54
ggtgatatct acggatttta cccta                                          26

<210> SEQ ID NO 55
<211> LENGTH: 27
<212> TYPE: DNA
<213> ORGANISM: Campylobacter jejuni

<400> SEQUENCE: 55
aatgggtatt cttggtgata tctacgg                                        27

<210> SEQ ID NO 56
<211> LENGTH: 41
<212> TYPE: DNA
<213> ORGANISM: Vibrio parahaemolyticus

<400> SEQUENCE: 56
tcagtttact tttttgggtt ttttggcttt catgaaacct g                        41

<210> SEQ ID NO 57
<211> LENGTH: 34
<212> TYPE: DNA
<213> ORGANISM: Vibrio parahaemolyticus

<400> SEQUENCE: 57
tcattaatgt tcacagtcat gtaggatgtc agcc                                34

<210> SEQ ID NO 58
<211> LENGTH: 24
<212> TYPE: DNA
<213> ORGANISM: Staphylococcus aureus

<400> SEQUENCE: 58
cacgcctgga gagccttcac cagc                                           24

<210> SEQ ID NO 59
```

```
<211> LENGTH: 30
<212> TYPE: DNA
<213> ORGANISM: Staphylococcus aureus

<400> SEQUENCE: 59
gttactgtaa tggcgctggt catgtagctg                                    30

<210> SEQ ID NO 60
<211> LENGTH: 30
<212> TYPE: DNA
<213> ORGANISM: Salmonella enterica

<400> SEQUENCE: 60
gaacaaccca tttgtattgg ttgttacggc                                    30

<210> SEQ ID NO 61
<211> LENGTH: 23
<212> TYPE: DNA
<213> ORGANISM: Salmonella enterica

<400> SEQUENCE: 61
ggctgctcgc ctttgctggt ttt                                           23

<210> SEQ ID NO 62
<211> LENGTH: 31
<212> TYPE: DNA
<213> ORGANISM: Bacillus cereus

<400> SEQUENCE: 62
catctgttga tgcggcttta aagggaaag t                                   31

<210> SEQ ID NO 63
<211> LENGTH: 30
<212> TYPE: DNA
<213> ORGANISM: Bacillus cereus

<400> SEQUENCE: 63
gagtcgcttt atcctttgca tctaccgcag                                    30

<210> SEQ ID NO 64
<211> LENGTH: 30
<212> TYPE: DNA
<213> ORGANISM: Bacillus cereus

<400> SEQUENCE: 64
cacctgccgg aggagcaaaa atgatacaac                                    30

<210> SEQ ID NO 65
<211> LENGTH: 31
<212> TYPE: DNA
<213> ORGANISM: Bacillus cereus

<400> SEQUENCE: 65
cagattcatt cttcgcttat ggtggtgact c                                  31

<210> SEQ ID NO 66
<211> LENGTH: 28
<212> TYPE: DNA
<213> ORGANISM: Escherichia coli

<400> SEQUENCE: 66
gatcagtatg gtcatgctgc gtttgagc                                      28
```

```
<210> SEQ ID NO 67
<211> LENGTH: 25
<212> TYPE: DNA
<213> ORGANISM: Escherichia coli

<400> SEQUENCE: 67
ggaatgcgga tctctttggt cacgc                                              25
```

FOOD-POISONING BACTERIA DETECTION CARRIER, AND METHOD FOR DETECTING FOOD-POISONING BACTERIA

RELATED APPLICATIONS

The present application is National Phase of International Application No. PCT/JP2011/002592 filed May 10, 2011, and claims priority from Japanese Application No. 2010-110293, filed May 12, 2010.

TECHNICAL FIELD

The invention relates to a carrier (e.g., microarray) for detecting food poisoning bacteria. In particular, the invention relates to a carrier and a method for detecting food poisoning bacteria that make it possible to specifically and simultaneously detect a plurality of types of food poisoning bacteria.

BACKGROUND ART

The presence or absence of food poisoning bacteria has been checked in the fields of food inspection, environmental inspection, clinical trial, animal health management, and the like. In recent years, a method that amplifies DNA contained in a sample by a polymerase chain reaction (PCR), and detect the target bacteria based on the amplified product has been employed.

Electrophoresis is widely used to detect food poisoning bacteria to determine the presence or absence of the target bacteria. The strain may be more accurately identified by purifying the detected amplified product, and performing a sequencing process.

However, the electrophoretic detection technique has a problem in that it is difficult to determine and identify the strain since it is difficult to identify bacteria having a similar amplification size. Moreover, the electrophoretic detection technique requires a complex operation such as gel preparation, and utilizes staining using a carcinogen (e.g., ethidium bromide). The electrophoretic detection technique also has a problem in that the sequencing process takes time, and requires an inconvenient operation.

Therefore, a detection technique using a DNA microarray has been used in recent years in addition to the electrophoretic detection technique. A probe that hybridizes to the target bacteria is immobilized on the DNA microarray. It is possible to determine the strain regardless of the amplification size by hybridizing the PCR amplified product to the probe. Moreover, the detection technique using the DNA microarray does not require staining using a carcinogen or the like, ensures prompt detection as compared with the sequencing process, and allows convenient operation.

A technique that detects the target bacteria by hybridizing the PCR amplified product to a probe by in situ hybridization or the like has also been used.

For example, Patent Document 1 discloses a probe and a DNA microarray that can detect *Alicyclobacillus acidocaldarius, Bacillus caldotenax, Bacillus cereus, Bacillus subtilis, Thermoactinomyces vulgaris*, and *Staphylococcus epidermidis*.

Patent Document 2 discloses a probe that can detect food poisoning bacteria (e.g., *Aeromonas bacteria, Listeria*, Welsh bacteria, *Vibrio parahaemolyticus, Salmonella*, and enteropathogenic *Escherichia coli*), and a method that detects food poisoning bacteria by in situ hybridization using the probe.
Patent Document 1: JP-A-2008-200012
Patent Document 2: JP-A-2006-166912

SUMMARY OF THE INVENTION

Technical Problem

*Escherichia coli, Listeria, Campylobacter, Vibrio parahaemolyticus, Staphylococcus aureus, Salmonella*, and *Bacillus cereus* cause 90% or more of bacterial food poisoning.

Therefore, it is very advantageous to make it possible to specifically and simultaneously detect whether seven types of these food poisoning bacteria are present in food, the environment, and the like.

It is necessary to use probes that exhibit excellent specificity in order to specifically and simultaneously detect a plurality of types of food poisoning bacteria. However, it is difficult to design such probes, and a DNA microarray or the like on which probes that can simultaneously detect a plurality of food poisoning bacteria are immobilized has not been proposed.

In view of the above situation, the inventors of the invention conducted extensive studies and numerous experiments, and developed probes that can specifically and simultaneously detect a toxin region gene or essential gene (eight genes (regions)) of *Escherichia coli, Listeria, Campylobacter, Vibrio parahaemolyticus, Staphylococcus aureus, Salmonella*, and *Bacillus cereus* to complete the invention.

Specifically, an object of the invention is to provide a carrier and a method for detecting food poisoning bacteria that can specifically and simultaneously detect two or more types of food poisoning bacteria among *Escherichia coli, Listeria, Campylobacter, Vibrio parahaemolyticus, Staphylococcus aureus, Salmonella*, and *Bacillus cereus*.

Solution to Problem

According to one aspect of the invention, there is provided a carrier for detecting food poisoning bacteria on which a plurality of probes are immobilized, the plurality of probes being selected, either alone or in combination, respectively from two or more groups among a first probe group for detecting *Escherichia coli* including probes that respectively have base sequences of SEQ ID NO: 1 to 6, and probes that respectively have base sequences complementary to the base sequences of SEQ ID NO: 1 to 6, a second probe group for detecting *Listeria* including probes that respectively have base sequences of SEQ ID NO: 7 to 13, and probes that respectively have base sequences complementary to the base sequences of SEQ ID NO: 7 to 13, a third probe group for detecting *Campylobacter* including probes that respectively have base sequences of SEQ ID NO: 14 to 19, and probes that respectively have base sequences complementary to the base sequences of SEQ ID NO: 14 to 19, a fourth probe group for detecting *Vibrio parahaemolyticus* including probes that respectively have base sequences of SEQ ID NO: 20 to 24, and probes that respectively have base sequences complementary to the base sequences of SEQ ID NO: 20 to 24, a fifth probe group for detecting *Staphylococcus aureus* including probes that respectively have base sequences of SEQ ID NO: 25 to 29, and probes that respectively have base sequences complementary to the base sequences of SEQ ID NO: 25 to 29, a sixth probe group for detecting *Salmonella* including probes that respectively have base sequences of SEQ ID NO: 30 to 40, and probes that respectively have base sequences complementary to the base sequences of SEQ ID NO: 30 to 40, and a seventh probe group for detecting *Bacillus cereus* including probes that respectively have base sequences of SEQ ID NO: 41 to 49, and probes that respectively have base sequences complementary to the base sequences of SEQ ID NO: 41 to 49.

According to another aspect of the invention, there is provided a method for detecting food poisoning bacteria including amplifying nucleic acid of food poisoning bacteria by PCR using a PCR reaction mixture that includes two or more primer sets, a genomic DNA sample, a nucleic acid polymerase, and a nucleic acid substrate to obtain an amplified product, when the genomic DNA sample contains genomic DNA of food poisoning bacteria that correspond to at least one of the two or more primer sets, and causing the amplified product to come in contact with a carrier for detecting food poisoning bacteria and hybridize to a probe immobilized on the carrier to detect the food poisoning bacteria, the two or more primer sets being selected from a group consisting of a first primer set for amplifying DNA of *Escherichia coli* including a primer having a base sequence of SEQ ID NO: 50 and a primer having a base sequence of SEQ ID NO: 51, a second primer set for amplifying DNA of *Listeria* including a primer having a base sequence of SEQ ID NO: 52 and a primer having a base sequence of SEQ ID NO: 53, a third primer set for amplifying DNA of *Campylobacter* including a primer having a base sequence of SEQ ID NO: 54 and a primer having a base sequence of SEQ ID NO: 55, a fourth primer set for amplifying DNA of *Vibrio parahaemolyticus* including a primer having a base sequence of SEQ ID NO: 56 and a primer having a base sequence of SEQ ID NO: 57, a fifth primer set for amplifying DNA of *Staphylococcus aureus* including a primer having a base sequence of SEQ ID NO: 58 and a primer having a base sequence of SEQ ID NO: 59, a sixth primer set for amplifying DNA of *Salmonella* including a primer having a base sequence of SEQ ID NO: 60 and a primer having a base sequence of SEQ ID NO: 61, a seventh primer set for amplifying DNA of *Bacillus cereus* including a primer having a base sequence of SEQ ID NO: 62 and a primer having a base sequence of SEQ ID NO: 63, and an eighth primer set for amplifying DNA of *Bacillus cereus* including a primer having a base sequence of SEQ ID NO: 64 and a primer having a base sequence of SEQ ID NO: 65, and a plurality of probes being immobilized on the carrier, the plurality of probes being selected, either alone or in combination, respectively from two or more groups among a first probe group for detecting *Escherichia coli* including probes that respectively have base sequences of SEQ ID NO: 1 to 6, and probes that respectively have base sequences complementary to the base sequences of SEQ ID NO: 1 to 6, a second probe group for detecting *Listeria* including probes that respectively have base sequences of SEQ ID NO: 7 to 13, and probes that respectively have base sequences complementary to the base sequences of SEQ ID NO: 7 to 13, a third probe group for detecting *Campylobacter* including probes that respectively have base sequences of SEQ ID NO: 14 to 19, and probes that respectively have base sequences complementary to the base sequences of SEQ ID NO: 14 to 19, a fourth probe group for detecting *Vibrio parahaemolyticus* including probes that respectively have base sequences of SEQ ID NO: 20 to 24, and probes that respectively have base sequences complementary to the base sequences of SEQ ID NO: 20 to 24, a fifth probe group for detecting *Staphylococcus aureus* including probes that respectively have base sequences of SEQ ID NO: 25 to 29, and probes that respectively have base sequences complementary to the base sequences of SEQ ID NO: 25 to 29, a sixth probe group for detecting *Salmonella* including probes that respectively have base sequences of SEQ ID NO: 30 to 40, and probes that respectively have base sequences complementary to the base sequences of SEQ ID NO: 30 to 40, and a seventh probe group for detecting *Bacillus cereus* including probes that respectively have base sequences of SEQ ID NO: 41 to 49, and probes that respectively have base sequences complementary to the base sequences of SEQ ID NO: 41 to 49, the two or more groups corresponding to the food poisoning bacteria that correspond to the two or more primer sets.

Advantageous Effects of the Invention

The invention thus makes it possible to specifically and simultaneously detect two or more types of food poisoning bacteria among *Escherichia coli, Listeria, Campylobacter, Vibrio parahaemolyticus, Staphylococcus aureus, Salmonella,* and *Bacillus cereus*.

BRIEF DESCRIPTION OF DRAWINGS

FIG. 1 is a view showing novel probes for detecting *Escherichia coli, Listeria, Campylobacter,* and *Vibrio parahaemolyticus* that are used for a carrier for detecting food poisoning bacteria according to one embodiment of the invention together with the detection target region, the SEQ ID NO., and the base sequence.

FIG. 2 is a view showing novel probes for detecting *Staphylococcus aureus, Salmonella,* and *Bacillus cereus* that are used for a carrier for detecting food poisoning bacteria according to one embodiment of the invention together with the detection target region, the SEQ ID NO., and the base sequence.

FIG. 3 is a view showing novel primer sets that are used for a method for detecting food poisoning bacteria according to one embodiment of the invention together with the amplification target region, the SEQ ID NO., and the base sequence.

FIG. 7 is a view showing the detection results (fluorescence intensity values) obtained using a carrier for detecting food poisoning bacteria according to one embodiment of the invention.

FIG. 11 is a view showing the simultaneous detection results (fluorescence intensity values) obtained using a carrier for detecting food poisoning bacteria according to one embodiment of the invention.

FIG. 12 is a matrix showing the detection results of novel probes used for a carrier for detecting food poisoning bacteria according to one embodiment of the invention.

FIG. 15 is a view showing detection results 1 (fluorescence intensity values) (i.e., the presence or absence of a false-positive reaction) obtained using a carrier for detecting food poisoning bacteria according to one embodiment of the invention.

FIG. 16 is a view showing detection results 2 (fluorescence intensity values) (i.e., the presence or absence of a false-positive reaction) obtained using a carrier for detecting food poisoning bacteria according to one embodiment of the invention.

DESCRIPTION OF EMBODIMENTS

Figure 4:
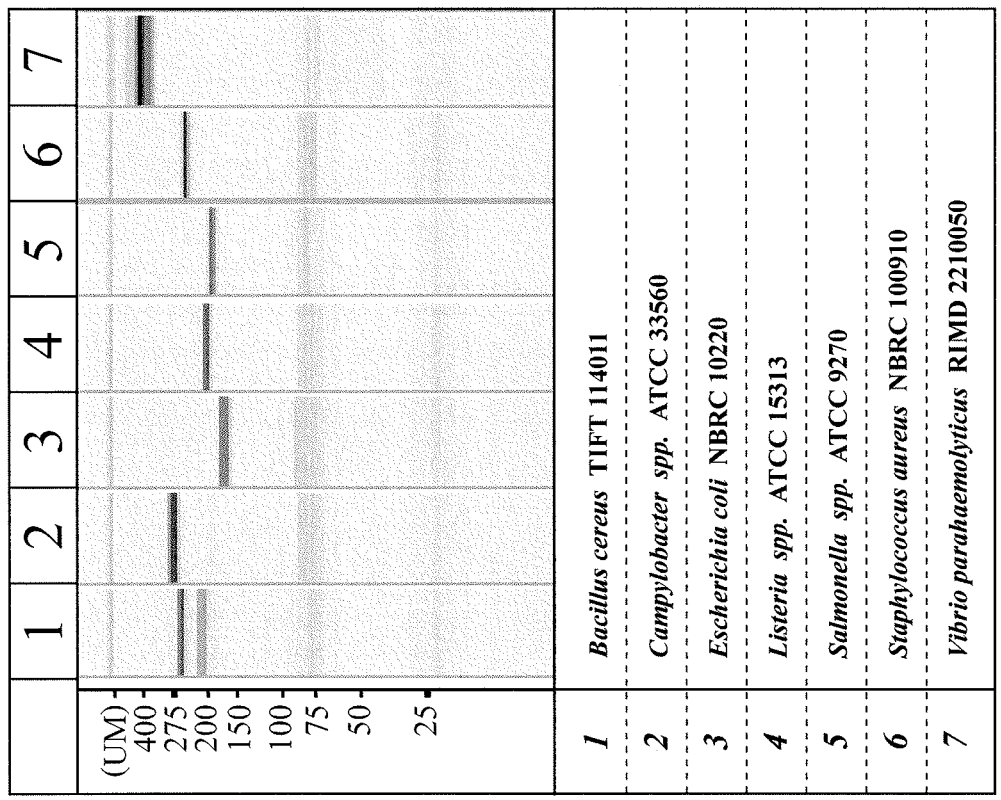
FIG. 4 is a view showing the amplification results for the DNA of the target food poisoning bacteria using a method for detecting food poisoning bacteria according to one embodiment of the invention.

Exemplary embodiments of the invention are described in detail below.

Probe

Probes used for a carrier and a method for detecting food poisoning bacteria according to the embodiments of the invention are described below with reference to FIGS. 1 and 2.

In FIGS. 1 and 2, the scientific name of food poisoning bacteria that are detected using each probe is listed in the column "Detection target food poisoning bacteria". The name of the gene in the detection target region of the corresponding food poisoning bacteria is listed in the column "Target region". The SEQ ID NO. and the base sequence listed in the Sequence Listing are listed in the columns "SEQ ID NO." and "Base sequence", respectively. The base sequence of each novel probe selected from the gene in the target region is listed in the column "Base sequence".

SEQ ID NO: 1 to 4 indicate the base sequences of probes for detecting a heat shock protein (dnaJ) gene of *Escherichia coli*.

SEQ ID NO: 5 and 6 indicate the base sequences of probes for detecting a uridine monophosphate kinase (pyrH) gene of *Escherichia coli*.

SEQ ID NO: 7 to 13 indicate the base sequences of probes for detecting a heat shock protein (dnaJ) gene of *Listeria*.

SEQ ID NO: 14 to 19 indicate the base sequences of probes for detecting a ribosomal (16S rRNA) gene of *Campylobacter*.

SEQ ID NO: 20 to 24 indicate the base sequences of probes for detecting a thermostable direct hemolysin (tdh) gene of *Vibrio parahaemolyticus*.

SEQ ID NO: 25 to 29 indicate the base sequences of probes for detecting a heat shock protein (dnaJ) gene of *Staphylococcus aureus*.

SEQ ID NO: 30 to 40 indicate the base sequences of probes for detecting an invasion (invA) gene of *Salmonella*.

SEQ ID NO: 41 to 45 indicate the base sequences of probes for detecting a non-hemolytic enterotoxin (nhe) gene of *Bacillus cereus*.

SEQ ID NO: 46 to 49 indicate the base sequences of probes for detecting a cereulide synthetase (cesB) gene of *Bacillus cereus*.

Each base sequence is written in the 5' to 3' direction.

Each probe used for the carrier and the method for detecting food poisoning bacteria according to the embodiments of the invention is not limited to the above base sequence. Each probe may be a probe having the corresponding base sequence wherein one or several bases are deleted, substituted, or added. Each probe may be a probe that hybridizes to a nucleic acid fragment having a base sequence complementary to the corresponding base sequence under stringent conditions. It is also possible to use a probe that has a base sequence complementary to that of such a probe or the probe having a base sequence among the base sequences of SEQ ID NO: 1 to 49.

The term "stringent conditions" used herein refers to conditions under which a specific hybrid is formed, but a non-specific hybrid is not formed. For example, the stringent conditions may be conditions under which DNA having high homology (90% or more, and preferably 95% or more) with DNA having a sequence among the sequences of SEQ ID NO: 1 to 49 hybridizes to DNA having a base sequence complementary to that of DNA having the sequence among the sequences of SEQ ID NO: 1 to 49. The stringent conditions normally refer to conditions under which hybridization occurs at a temperature lower than the melting temperature (Tm) of a perfect hybrid by about 5° C. to about 30° C. (preferably about 10° C. to about 25° C.). For example, the conditions described in J. Sambrook et al., Molecular Cloning, A Laboratory Manual, Second Edition, Cold Spring Harbor Laboratory Press (1989) (particularly the conditions described in §11.45 "Conditions for Hybridization of Oligonucleotide Probes") may be used as the stringent conditions.

Each probe used for the carrier and the method for detecting food poisoning bacteria according to the embodiments of the invention has a length of about 20 mer to about 33 mer (bases), and may be synthesized using a DNA synthesizer.

Carrier for Detecting Food Poisoning Bacteria

The carrier for detecting food poisoning bacteria according to the embodiment of the invention is a medium device for detecting specific food poisoning bacteria, and may be implemented by a microarray or the like.

The carrier is not particularly limited as long as at least one of the probes for detecting the detection target food poisoning bacteria is immobilized on the carrier. For example, a spot-type DNA microarray, a synthesis-type DNA microarray, or the like may be used as the carrier.

The carrier according to the embodiment of the invention may be produced by a normal method using a probe having a sequence among the sequences of SEQ ID NO: 1 to 49.

For example, a spot-type DNA microarray may be produced as the carrier according to the embodiment of the invention by immobilizing a probe on a slide using a DNA spotter. A synthesis-type DNA microarray may be produced as the carrier according to the embodiment of the invention by synthesizing a single-stranded oligo-DNA having the above sequence on a glass substrate using a photolithographic technique to prepare a probe.

PCR Primer

A PCR primer used for the method for detecting food poisoning bacteria according to the embodiment of the invention is described below with reference to FIG. 3.

The PCR primer is used to amplify a region (part) of genomic DNA in a sample (hereinafter may be referred to as "genomic DNA sample" or "DNA sample") by PCR. More specifically, the PCR primer is used to amplify a region specified by a forward primer and a reverse primer (i.e., PCR primer set). The PCR primer set is added to a PCR reaction mixture. The PCR reaction mixture includes a nucleic acid substrate, a nucleic acid polymerase, a genomic DNA sample, a labeling component, a buffer solution, and the like in addition to the PCR primer set. A region (part) of the genomic DNA sample may be amplified using the PCR reaction mixture utilizing a nucleic acid amplification system (e.g., thermal cycler). More specifically, when the sample contains genomic DNA having a target region (amplification target region) that is amplified using the PCR primer set, the target region is amplified. The PCR primer set used in connection with the embodiment of the invention may be used for normal PCR.

In FIG. 3, the scientific name of food poisoning bacteria that are amplified using each PCR primer set is listed in the column "Amplification target food poisoning bacteria". The name of the gene in the amplification target region of the corresponding food poisoning bacteria is listed in the column "Target region". The length (bp (base pairs)) of the base sequence of the amplified product obtained by amplifying the corresponding target region using the PCR primer set is listed in the column "Amplified product". The SEQ ID NO. of each base sequence listed in the Sequence Listing is listed in the column "SEQ ID NO.". The column "F/R" indicates whether the primer is a forward primer or a reverse primer (F: forward primer, R: reverse primer). Each base sequence listed in the Sequence Listing is listed the column "Base sequence". The base sequence of each novel primer set designed to specifically amplify the corresponding target region is listed in the column "Base sequence".

SEQ ID NO: 50 and 51 indicate the base sequences of the primer set for amplifying a uridine monophosphate kinase (pyrH) gene in the essential region contained in genomic DNA of *Escherichia coli*. The length of the amplified product is 157 bp.

SEQ ID NO: 52 and 53 indicate the base sequences of the primer set for amplifying a heat shock protein (dnaJ) gene in the essential region contained in genomic DNA of *Listeria*. The length of the amplified product is 176 bp.

SEQ ID NO: 54 and 55 indicate the base sequences of the primer set for amplifying a ribosomal (16S rRNA) gene in the essential region contained in genomic DNA of *Campylobacter*. The length of the amplified product is 263 bp.

SEQ ID NO: 56 and 57 indicate the base sequences of the primer set for amplifying a thermostable direct hemolysin (tdh) gene in the toxin region contained in genomic DNA of *Vibrio parahaemolyticus*. The length of the amplified product is 380 bp.

SEQ ID NO: 58 and 59 indicate the base sequences of the primer set for amplifying a heat shock protein (dnaJ) gene in the essential region contained in genomic DNA of *Staphylococcus aureus*. The length of the amplified product is 236 bp.

SEQ ID NO: 60 and 61 indicate the base sequences of the primer set for amplifying an invasion (invA) gene in the toxin region contained in genomic DNA of *Salmonella*. The length of the amplified product is 180 bp.

SEQ ID NO: 62 and 63 indicate the base sequences of the primer set for amplifying a non-hemolytic enterotoxin (nhe) gene in the toxin region contained in genomic DNA of *Bacillus cereus*. The length of the amplified product is 195 bp.

SEQ ID NO: 64 and 65 indicate the base sequences of the primer set for amplifying a cereulide synthetase (cesB) gene in the toxin region contained in genomic DNA of *Bacillus cereus*. The length of the amplified product is 238 bp.

Each base sequence is written in the 5' to 3' direction.

Each primer of the PCR primer set according to the embodiment of the invention is not limited to the above base sequence. Each primer may be a primer having the corresponding base sequence wherein one or several bases are deleted, substituted, or added. Each primer may be a primer that includes a nucleic acid fragment that hybridizes to a nucleic acid fragment having a base sequence complementary to the corresponding base sequence under stringent conditions.

It is also possible to use a PCR primer set that includes primers respectively having a base sequence complementary to the PCR primer set according to the embodiment of the invention.

When the sample included in the PCR reaction mixture contains genomic DNA of one type of the amplification target food poisoning bacteria, and a PCR amplification reaction is effected using the PCR reaction mixture that includes the above eight PCR primer sets, the amplification target region of the genomic DNA can be specifically amplified.

When the sample contains genomic DNA of two or more types of the amplification target food poisoning bacteria, the amplification target region of each genomic DNA can be simultaneously and specifically amplified.

When the sample contains genomic DNA (i.e., eight genes) of all types (seven types) of the amplification target food poisoning bacteria, the amplification target region of each genomic DNA can be specifically and simultaneously amplified using the carrier and the method for detecting food poisoning bacteria according to the embodiments of the invention.

Specifically, when using the PCR primer set used for the method for detecting food poisoning bacteria according to the embodiment of the invention, genomic DNA other than genomic DNA of the target food poisoning bacteria is not amplified. Moreover, non-specific amplification due to a combination of primers included in different primer sets does not occur even when using a plurality of PCR primer sets in combination.

Therefore, when the sample contains genomic DNA of food poisoning bacteria having the amplification target region, the amplification target region can be specifically amplified by adding the PCR primer set to the PCR reaction mixture.

Moreover, the amplification target region of each genomic DNA can be specifically and simultaneously amplified even when the sample contains a plurality of types of the amplification target food poisoning bacteria.

When the PCR reaction mixture includes one to seven PCR primer sets among the eight PCR primer sets, the target region can also be specifically amplified when the PCR reaction mixture contains genomic DNA of food poisoning bacteria having the amplification target region.

PCR Reaction Mixture

The PCR reaction mixture used for the method for detecting food poisoning bacteria according to the embodiment of the invention is described below.

The PCR reaction mixture includes at least one PCR primer set among the eight PCR primer sets. The PCR reaction mixture preferably includes two or more PCR primer sets among the eight PCR primer sets, and more preferably includes all of the eight PCR primer sets. The PCR reaction mixture may include commonly-used components in addition to the PCR primer set(s).

For example, the PCR reaction mixture may have the following composition. Note that the composition of the PCR reaction mixture is not limited thereto. In particular, the volume of the primers, the DNA sample, and sterilized water varies depending on the number of types of amplification target food poisoning bacteria.
Buffer solution (10 vol %)
Nucleic acid substrate (8 vol %)
Forward primer (10 ng/μl, 2 to 16 vol %)
Reverse primer (10 ng/μl, 2 to 16 vol %)
Nucleic acid polymerase (0.5 vol %)
Labeling component Cy5 (10 pmol/μl, 1 to 8 vol %)
DNA sample (5 to 35 vol %)
Water (6.5 to 71.5 vol %)

Method for Detecting Food Poisoning Bacteria

The method for detecting food poisoning bacteria according to the embodiment of the invention is described below.

Genomic DNA contained in the sample is amplified by PCR using the PCR reaction mixture.

When detecting food poisoning bacteria in practice, a sample is collected from food, facilities (equipment), or the like, and bacteria contained in the sample are cultured. Genomic DNA is extracted from the cultured bacteria, and used as the sample included in the PCR reaction mixture. Therefore, it is unknown whether or not the amplification target food poisoning bacteria are present in the sample in practice. The amplification target food poisoning bacteria can be detected by the method for detecting food poisoning bacteria according to the embodiment of the invention when the amplification target food poisoning bacteria are present in the sample. When the PCR reaction mixture includes all of the eight PCR primer sets, and at least one gene among the eight genes (regions) of the seven types of bacteria is present in the sample, the amplification target region can be specifically amplified.

A nucleic acid amplification system is used when amplifying a gene by PCR. A normal thermal cycler or the like may be used as the nucleic acid amplification system. PCR may be performed under the following conditions, for example. Note that the PCR conditions are not limited thereto.
(1) 95° C./2 min
(2) 95° C./10 sec (DNA strand separation step (denaturation step))
(3) 68° C./30 sec (annealing step)
(4) 72° C./30 sec (DNA extension step)
(5) 72° C./2 min
The steps (2) to (4) are repeated in 40 cycles.

The resulting PCR amplified product is added dropwise to the carrier for detecting food poisoning bacteria according to the embodiment of the invention, and the label of the PCR amplified product that has hybridized to the probe immobilized on the carrier is detected.

More specifically, the following operation is performed, for example.

A given buffer solution is mixed with the PCR amplified product, and the mixture is added dropwise to the carrier.

After allowing the carrier to stand at 45° C. for 1 hour, the PCR amplified product that has not hybridized is washed away from the carrier using the buffer solution.

The carrier is installed in a label detection system to detect the label to detect whether or not the target food poisoning bacteria are present in the sample.

Probe Design

A probe design method that was contrived to improve the specificity of each probe used for the carrier and the method for detecting food poisoning bacteria according to the embodiments of the invention is described below.

The probes are used to specifically and simultaneously detect the eight regions of the seven types of food poisoning bacteria. The probes used in connection with the embodiments of the invention are required to exhibit high specificity in order to specifically detect such a number of targets. The inventors conducted studies in order to implement a probe design method that can improve the specificity of each probe, and found that the specificity of each probe can be improved by satisfying the following requirements.

(1) GC Content

A probe having a base sequence having a GC content of 40% or less is used. The probe more easily dissociates when the GC content is lower than the AT content by a specific value. This makes it possible to reduce non-specific binding during hybridization, so that the specificity of the probe can be improved. Note that the GC content indicates the percentage of the number of GC contained in the base sequence of the probe.

(2) Select Probe from 3'-End Region of PCR Amplification Target Region

The sense-strand probe (i.e., a probe selected from the sense strand of the amplification target region) is selected from the 3'-end half region of the PCR amplified product (detection target). Specifically, the sense-strand probe is selected from the 3'-end half region of the amplification target region that is amplified by the primer set for the food poisoning bacteria that are detected by the probe.

This makes it possible to increase the fluorescence intensity as compared with the case of selecting the probe from the 5'-end half region.

It is preferable to select the antisense-strand probe (i.e., a probe selected from the antisense strand of the amplification target region) from the 5'-end half region of the complementary sequence of the amplification target region that is amplified by the primer set for the food poisoning bacteria that are detected by the probe.

(3) Set Consecutive Match Count with Non-Target Base Sequence to 12 Bases or Less The probe is designed so that the consecutive match count with a gene sequence of non-target bacteria or the like is 12 bases or less.

In the method for detecting food poisoning bacteria according to the embodiment of the invention, hybridization aimed at the amplified products of the eight regions of the seven types of food poisoning bacteria is performed. Therefore, it is preferable to design each probe so that the consecutive match count with at least the sequences of the seven regions other than the detection target region is 12 bases or less.

Each probe used for the carrier and the method for detecting food poisoning bacteria according to the embodiments of the invention is designed taking account of the above requirements so that non-specific hybridization does not occur in the eight regions of the seven types of food poisoning bacteria.

It is possible to improve the specificity (i.e., a capability to specifically hybridize to the detection target gene region) of each probe as compared with a known probe by designing the each probe to meet at least one of the requirements (1) to (3).

The carrier and the method for detecting food poisoning bacteria according to the embodiments of the invention can specifically and simultaneously detect the eight regions of the seven types of food poisoning bacteria by designing the probes to meet all of the requirements (1) to (3).

(4) Detection Target Region

The probes used in connection with the embodiments of the invention are selected (designed) from the specific region of the respective food poisoning bacteria (see FIGS. 1 and 2).

Specifically, the probes aim at the gene in the toxin region and/or the essential region of the respective food poisoning bacteria.

More specifically, a heat shock protein (dnaJ) gene and a uridine monophosphate kinase (pyrH) gene are selected as the detection target region of *Escherichia coli*, a heat shock protein (dnaJ) gene is selected as the detection target region of *Listeria*, a ribosomal (16S rRNA) gene is selected as the detection target region of *Campylobacter*, a thermostable direct hemolysin (tdh) gene is selected as the detection target region of *Vibrio parahaemolyticus*, a heat shock protein (dnaJ) gene is selected as the detection target region of *Staphylococcus aureus*, an invasion (invA) gene is selected as the detection target region of *Salmonella*, and a non-hemolytic enterotoxin (nhe) gene and a cereulide synthetase (cesB) gene are selected as the detection target region of *Bacillus cereus*.

The specificity of each probe used for the carrier and the method for detecting food poisoning bacteria according to the embodiments of the invention can be improved by selecting each probe from the above detection target regions.

The carrier and the method for detecting food poisoning bacteria according to the embodiments of the invention can thus specifically and simultaneously detect the eight regions of the seven types of food poisoning bacteria (i.e., *Escherichia coli*, *Listeria*, *Campylobacter*, *Vibrio parahaemolyticus*, *Staphylococcus aureus*, *Salmonella*, and *Bacillus cereus*).

It is possible to design probes that exhibit high specificity by utilizing the probe design method according to the embodiment of the invention.

EXAMPLES

Experiments were performed in order to check whether or not the amplification target region can be correctly amplified using the PCR primer set used for the method for detecting food poisoning bacteria according to the embodiment of the invention.

Specifically, a PCR amplification reaction was effected by the above method using a PCR reaction mixture containing the PCR primer set used in connection with the embodiment of the invention, and the amplified product was subjected to electrophoresis to check whether or not a correct amplified product was obtained.

Experiment 1

A PCR reaction mixture having the following composition was used. The primers (primerF (forward) and primerR (reverse)) were synthesized by Life Technologies Japan Ltd. The other components are products manufactured by Takara Bio Inc.
Buffer solution "10×Ex Taq buffer" (20 mM Mg 2+ plus): 2.0 µl
Nucleic acid substrate "dNTP Mixture" (2.5 mM dATP, 2.5 mM dCTP, 2.5 mM dGTP, and 2.5 mM dTTP): 1.6 µl
primerF (10 ng/µl, final conc.: 4 ng): 0.4 µl
primerR (10 ng/µl, final conc.: 4 ng): 0.4 µl
Nucleic acid polymerase "EX Taq" (5 U/µl): 0.1 µl
Labeling component "Cy5": 0.2 µl
DNA sample (1 ng/µl): 1.0 µl
Sterilized water: 14.3 µl
(Total amount: 20 µl)

The primer sets shown in FIG. 3 were used for the respective amplification target food poisoning bacteria. The following food poisoning bacteria strains were used as the DNA sample corresponding to each primer set. A PCR amplification reaction was effected corresponding to the respective food poisoning bacteria.
1. *Bacillus cereus* TIFT 114011
2. *Campylobacter jejuni* ATCC 33560
3. *Escherichia coli* NBRC 102203
4. *Listeria monocytogenes* ATCC 15313
5. *Salmonella enterica* ATCC 9270
6. *Staphylococcus aureus* NBRC 100910
7. *Vibrio parahaemolyticus* RIMD 2210050

These food poisoning bacteria strains were transferred from the following organizations.
Toyo Institute of Food Technology (TIFT)
American Type Culture Collection (ATCC)
Biological Resource Center (NBRC), National Institute of Technology and Evaluation Research Institute for Microbial Diseases (RIMD), Osaka University PCR gene amplification was performed for each sample under the following conditions using a system "Mastercycler ep gradient" (manufactured by Eppendorf).
(1) 95° C./2 min
(2) 95° C./10 sec (DNA strand separation step (denaturation step))
(3) 68° C./30 sec (annealing step)
(4) 72° C./30 sec (DNA extension step)
(5) 72° C./2 min
The steps (2) to (4) were repeated in 40 cycles.

The PCR amplified product was subjected to electrophoresis to check whether or not a correct amplified product was obtained. Electrophoresis was performed using an electrophoresis system "MultiNA" (manufactured by Shimadzu Corporation). The results are shown in FIG. 4.

The bands (lanes 1 to 7) shown in FIG. 4 indicate the electrophoresis results when subjecting each PCR amplified product obtained using the PCR reaction mixture containing genomic DNA of the corresponding food poisoning bacteria to electrophoresis.

When subjecting the PCR amplified product to electrophoresis, the base sequence of the PCR amplified product may not completely coincide with the theoretical base sequence (i.e., approximate results are obtained) due to a measurement error of the system.

As shown in FIG. 4, bands were observed at around 200 bp and 250 bp when using the strain 1 (genomic DNA of *Bacillus cereus*) as the DNA sample.

It was thus confirmed that the amplification target region of a non-hemolytic enterotoxin (nhe) gene and the amplification target region of a cereulide synthetase (cesB) gene of *Bacillus cereus* could be amplified.

A band was observed at around 275 bp when using the strain 2 (genomic DNA of *Campylobacter*) as the DNA sample. It was thus confirmed that the amplification target region of a ribosomal (16S rRNA) gene of *Campylobacter* could be amplified.

A band was observed at around 160 bp when using the strain 3 (genomic DNA of *Escherichia coli*) as the DNA sample. It was thus confirmed that the amplification target region of a uridine monophosphate kinase (pyrH) gene of *Escherichia coli* could be amplified.

A band was observed at around 200 bp when using the strain 4 (genomic DNA of *Listeria*) as the DNA sample. It was thus confirmed that the amplification target region of a heat shock protein (dnaJ) gene of *Listeria* could be amplified.

Note that the length of the amplified product the strain 4 differs from the length (176 bp) of the theoretical amplified product of a heat shock protein gene of *Listeria* by about 20 bp. It is considered that the above difference occurred due to insertion of a sequence into the heat-shock protein (dnaJ) gene of the strain 4.

A band was observed at around 190 bp when using the strain 5 (genomic DNA of *Salmonella*) as the DNA sample. It was thus confirmed that the amplification target region of an invasion (invA) gene of *Salmonella* could be amplified.

A band was observed at around 240 bp when using the strain 6 (genomic DNA of *Staphylococcus aureus*) as the DNA sample. It was thus confirmed that the amplification target region of a heat shock protein (dnaJ) gene of *Staphylococcus aureus* could be amplified.

A band was observed at around 400 bp when using the strain 7 (genomic DNA of *Vibrio parahaemolyticus*) as the DNA sample. It was thus confirmed that the amplification target region of a thermostable direct hemolysin (tdh) gene of *Vibrio parahaemolyticus* could be amplified.

It was confirmed by the above results that the amplification target region of the food poisoning bacteria as the detection target of each probe used for the carrier and the method for detecting food poisoning bacteria according to the embodiments of the invention was appropriately amplified to obtain a PCR amplified product corresponding to each region.

Example 1

Experiments were performed using each PCR amplified product in order to check whether or not the detection target food poisoning bacteria can be detected by each probe immobilized on the carrier for detecting food poisoning bacteria according to the embodiment of the invention.

Figure 5:
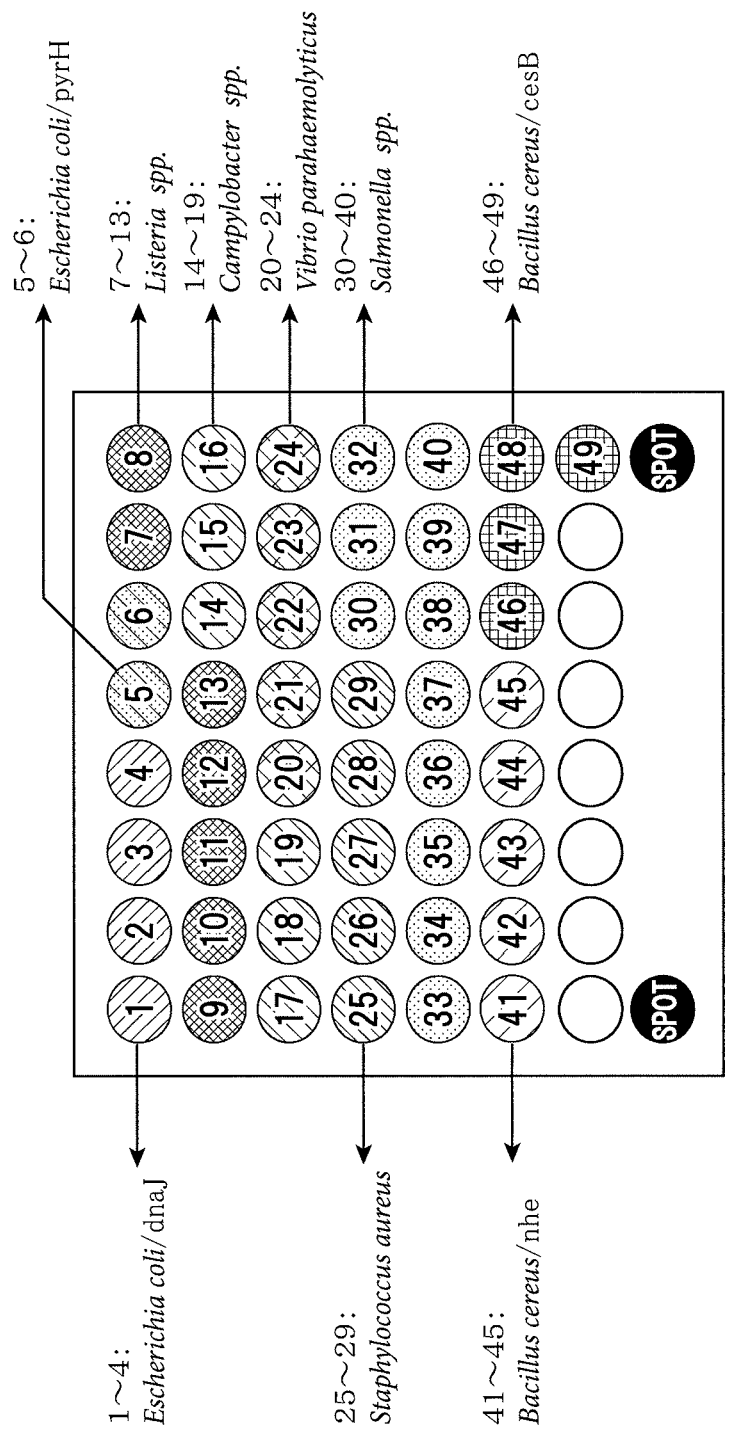
FIG. 5 is a view showing the arrangement of probes respectively having base sequences of SEQ ID NO: 1 to 49 on a carrier for detecting food poisoning bacteria according to one embodiment of the invention.

A carrier on which probes were immobilized as shown in FIG. 5 was used as the carrier for detecting food poisoning bacteria according to the embodiment of the invention. Specifically, probes (SEQ ID NO: 1 to 4) for detecting a heat shock protein gene of *Escherichia coli* were immobilized on spots 1 to 4. Probes (SEQ ID NO: 5 and 6) for detecting a uridine monophosphate kinase gene of *Escherichia coli* were immobilized on spots 5 and 6. Probes (SEQ ID NO: 7 to 13) for detecting a heat shock protein gene of *Listeria* were immobilized on spots 7 to 13. Probes (SEQ ID NO: 14 to 19) for detecting a ribosomal gene of *Campylobacter* were immobilized on spots 14 to 19. Probes (SEQ ID NO: 20 to 24) for detecting a thermostable direct hemolysin gene of *Vibrio parahaemolyticus* were immobilized on spots 20 to 24. Probes (SEQ ID NO: 25 to 29) for detecting a heat shock protein gene of *Staphylococcus aureus* were immobilized on spots 25 to 29. Probes (SEQ ID NO: 30 to 40) for detecting an invasion gene of *Salmonella* were immobilized on spots 30 to 40. Probes (SEQ ID NO: 41 to 45) for detecting a non-hemolytic enterotoxin gene contained in the genome of *Bacillus cereus* were immobilized on spots 41 to 45. Probes (SEQ ID NO: 46 to 49) for detecting a cereulide synthetase gene contained in the genome of *Bacillus cereus* were immobilized on spots 46 to 49.

The PCR amplified product obtained in Experiment 1 was added dropwise to the carrier corresponding to the respective food poisoning bacteria, and the label of the PCR amplified product that had hybridized to the probe immobilized on the carrier was detected. A PCR amplified product was also used that was obtained in the same manner as in Experiment 1, except that the genomic DNA of *Escherichia coli* (strain 3) was used as the DNA sample, and the primer pair having the base sequence of SEQ ID NO: 66 and 67 (amplification target region: dnaJ, length of amplified product: 218 bp) was used as the primers. More specifically, the following operation was performed.

A solution prepared by adding 0.3% SDS (sodium dodecyl sulfate) to a buffer solution (3×SSC citric acid-physiological saline solution) was mixed with the PCR amplified product, and the mixture was added dropwise to the microarray.

The microarray was allowed to stand at 45° C. for 1 hour. The PCR amplified product that did not hybridize was washed away from the microarray using the buffer solution.

Figure 6:
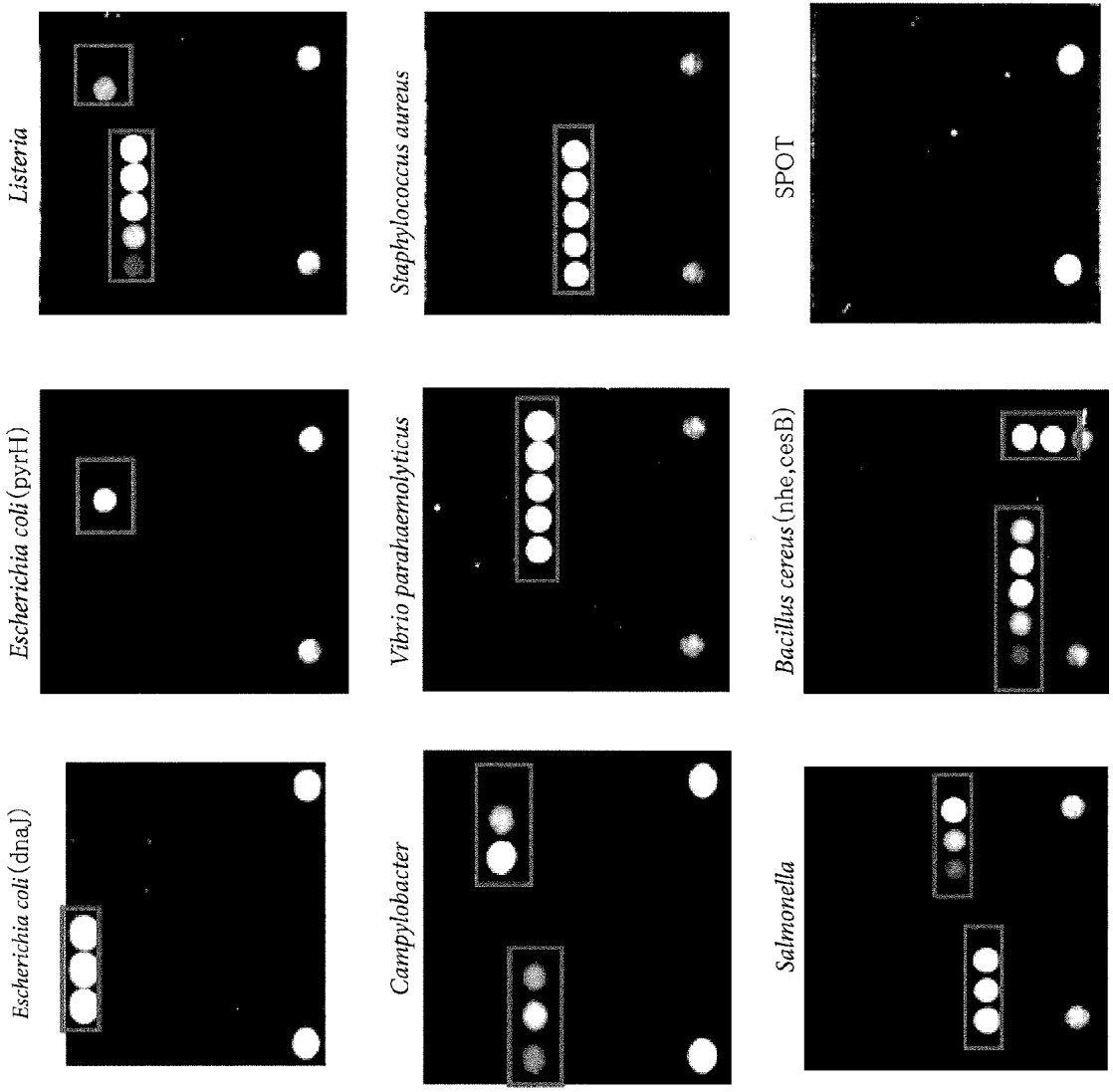
FIG. 6 is a view showing the detection results (fluorescence photographs) obtained using a carrier for detecting food poisoning bacteria according to one embodiment of the invention.

The microarray was installed in a label detection system ("BIOSHOT" manufactured by Toyo Kohan Co., Ltd.) to measure the fluorescence intensity. Specifically, the labeling component (Cy5) was caused to emit light by laser light excitation, and the intensity of light was detected and captured using a CCD camera mounted in the detector. The results are shown in FIG. 6. The intensity of light was converted into electrical signals, and the electrical signals were converted into numerical values to obtain the fluorescence intensity. The results are shown in FIG. 7. The fluorescence intensity (no unit) is an intensity index specific to the system, and is calculated by correcting the values so that the background value is zero.

In FIGS. 6 and 7, "*Escherichia coli*" indicates the results obtained by hybridization of the PCR amplified product (amplified products of dnaJ and pyrH) of the strain 3 (*Escherichia coli* NBRC 102203), "*Listeria*" indicates the results obtained by hybridization of the PCR amplified product of the strain 4 (*Listeria monocytogenes* ATCC 15313), "*Campylobacter*" indicates the results obtained by hybridization of the PCR amplified product of the strain 2 (*Campylobacter jejuni* ATCC 33560), "*Vibrio parahaemolyticus*" indicates the results obtained by hybridization of the PCR amplified product of the strain 7 (*Vibrio parahaemolyticus* RIMD 2210050), "*Staphylococcus aureus*" indicates the results obtained by hybridization of the PCR amplified product of the strain 6 (*Staphylococcus aureus* NBRC 100910), "*Salmonella*" indicates the results obtained by hybridization of the PCR amplified product of the strain 5 (*Salmonella enterica* ATCC 9270), and "*Bacillus cereus*" indicates the results obtained by hybridization of the PCR amplified product of the strain 1 (*Bacillus cereus* TIFT 114011).

As shown in FIG. 6, fluorescence was clearly detected for *Escherichia coli* from the spots 2 to 4 and 6. As shown in FIG. 7, a constant fluorescence intensity value was obtained (i.e., fluorescence was detected) from the spots 1 and 5. It was thus confirmed that *Escherichia coli* can be detected using the carrier for detecting food poisoning bacteria according to the embodiment of the invention when the PCR amplified product contains the amplified product of a heat shock protein gene or a uridine monophosphate kinase gene of *Escherichia coli*.

Note that the PCR amplified product may be a nucleic acid fragment having a base sequence complementary to that of a nucleic acid fragment that hybridizes to each probe. Therefore, a probe having a base sequence complementary to a base sequence among the base sequences of SEQ ID NO: 1 to 6 can hybridize to a nucleic acid fragment having such a complementary base sequence. Accordingly, *Escherichia coli* can also be detected when a probe having a base sequence complementary to a base sequence among the base sequences of SEQ ID NO: 1 to 6 is immobilized on the carrier for detecting food poisoning bacteria according to the embodiment of the invention. This also applies to the other food poisoning bacteria.

As shown in FIG. 6, fluorescence was clearly detected for *Listeria* from the spots 7 and 9 to 13. As shown in FIG. 7, a constant fluorescence intensity value was obtained (i.e., fluorescence was detected) from the spot 8. It was thus confirmed that *Listeria* can be detected using the carrier for detecting food poisoning bacteria according to the embodiment of the invention when the PCR amplified product contains the amplified product of a heat shock protein gene of *Listeria*. Note that the probe immobilized on the spot 7 was an antisense-strand probe (i.e., a probe having a base sequence complementary to the base sequence of SEQ ID NO: 7).

As shown in FIG. 6, fluorescence was clearly detected for *Campylobacter* from the spots 14 to 19. FIG. 7 also shows that fluorescence was detected from the spots 14 to 19. It was thus confirmed that *Listeria* can be detected using the carrier for detecting food poisoning bacteria according to the embodiment of the invention when the PCR amplified product contains the amplified product of a heat shock protein gene of *Listeria*. Note that the probes immobilized on the spots 14 and 15 were antisense-strand probes (i.e., probes having a base sequence complementary to the base sequence of SEQ ID NO: 14 or 15).

As shown in FIG. 6, fluorescence was clearly detected for *Vibrio parahaemolyticus* from the spots 20 to 24. FIG. 7 also shows that fluorescence was detected from the spots 20 to 24. It was thus confirmed that *Vibrio parahaemolyticus* can be detected using the carrier for detecting food poisoning bacteria according to the embodiment of the invention when the PCR amplified product contains the amplified product of a thermostable direct hemolysin gene of *Vibrio parahaemolyticus*.

As shown in FIG. 6, fluorescence was clearly detected for *Staphylococcus aureus* from the spots 25 to 29. FIG. 7 also shows that fluorescence was detected from the spots 25 to 29. It was thus confirmed that *Staphylococcus aureus* can be detected using the carrier for detecting food poisoning bacteria according to the embodiment of the invention when the PCR amplified product contains the amplified product of a heat shock protein gene of *Staphylococcus aureus*.

As shown in FIG. 6, fluorescence was clearly detected for *Salmonella* from the spots 30 to 35. As shown in FIG. 7, a constant fluorescence intensity value was obtained (i.e., fluorescence was detected) from the spots 36 to 40. It was thus confirmed that *Salmonella* can be detected using the carrier for detecting food poisoning bacteria according to the embodiment of the invention when the PCR amplified product contains the amplified product of an invasion gene of *Salmonella*.

As shown in FIG. 6, fluorescence was clearly detected for *Bacillus cereus* from the spots 41 to 45, 48, and 49. As shown in FIG. 7, a constant fluorescence intensity value was obtained (i.e., fluorescence was detected) from the spots 46 and 47. It was thus confirmed that *Bacillus cereus* can be detected using the carrier for detecting food poisoning bacteria according to the embodiment of the invention when the PCR amplified product contains the amplified product of a non-hemolytic enterotoxin gene or a cereulide synthetase gene of *Bacillus cereus*.

It was confirmed by the above results that the PCR amplified product of food poisoning bacteria that hybridizes to each probe can be appropriately detected using the carrier and the method for detecting food poisoning bacteria according to the embodiments of the invention when the PCR amplified product contains such a PCR amplified product.

Relationship Between Position of Probe in PCR Amplification Target Region and Fluorescence Intensity The effects of the position of the probe in the PCR amplification target region on the fluorescence intensity are discussed below with reference to FIG. 8A, FIG. 8B, and FIG. 8C.

The probe is designed by selecting a base sequence that can specifically detect the detection target food poisoning bacteria from the amplification target region (i.e., a region amplified by the primer set) of the gene of the detection target food poisoning bacteria.

Therefore, experiments were performed in order to determine the relationship between the position of the probe in the amplification target region and the fluorescence intensity.

Experiment 2

A plurality of probes that respectively hybridize to various positions of a heat shock protein gene (amplification target region) of *Listeria* were prepared. The genomic DNA of *Listeria* was amplified using the primer set having the base sequences of SEQ ID NO: 52 and 53. Each probe was hybridized to the resulting amplified product, and the fluorescence intensity was measured in the same manner as in Example 1. The results are shown in FIG. 8A.

Figure 8B:
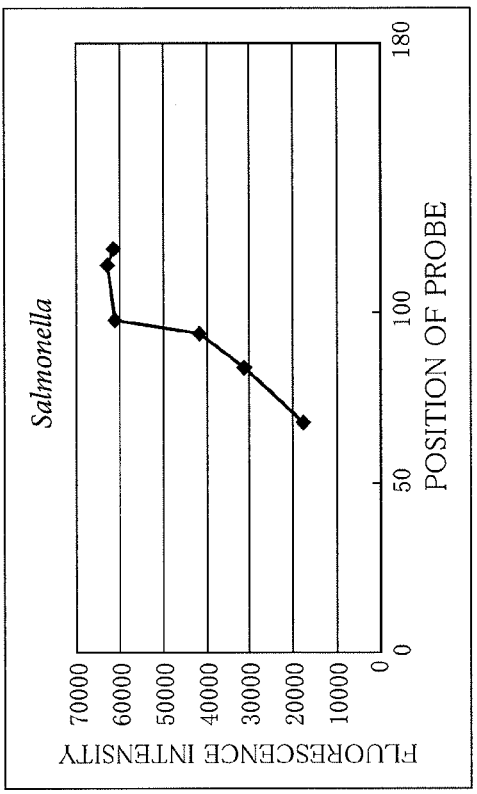
FIG. 8A, FIG. 8B, and FIG. 8C are graphs respectively showing the relationship between the position of a probe in a PCR amplification target region and fluorescence intensity.
Figure 8A:
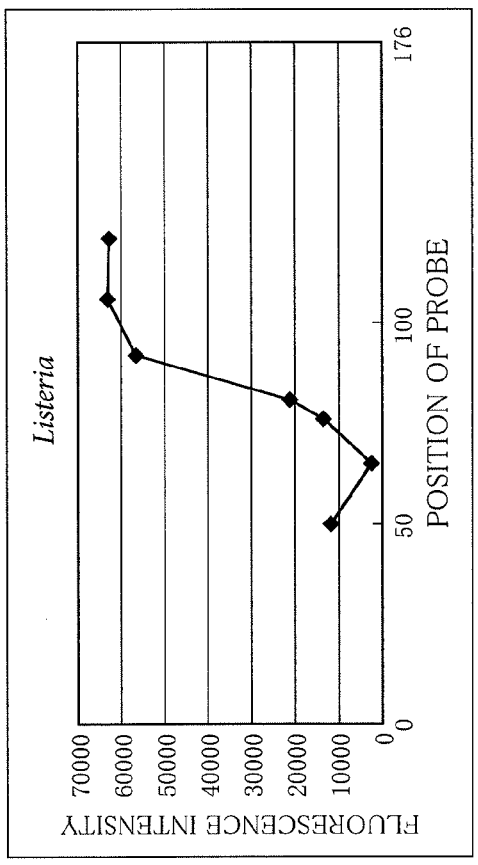
Figure 8C:
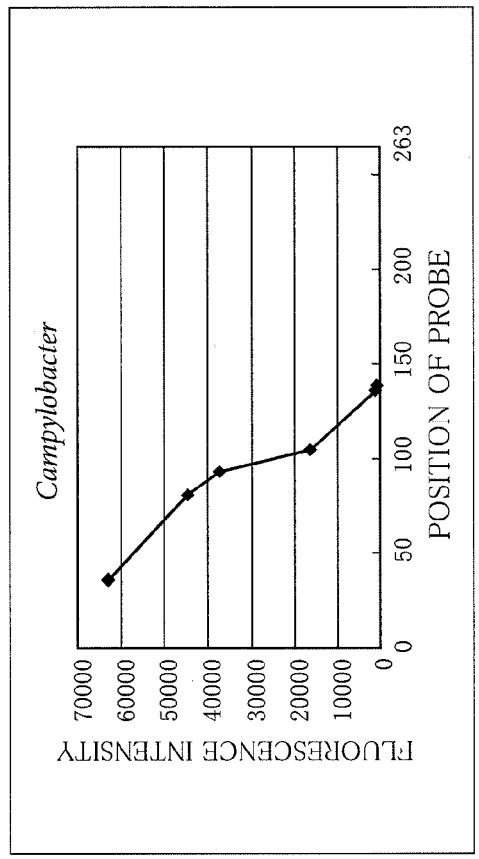

In FIG. 8A, FIG. 8B, and FIG. 8C, the vertical axis indicates the fluorescence intensity, and the horizontal axis indicates the position of the probe in the amplification target region. The left end (0) of the horizontal axis indicates the 5'-end of the amplification target region, the right end (176 in FIG. 8A) of the horizontal axis indicates the 3'-end of the amplification target region, and each plot indicates the position of the 3'-end of the probe that hybridizes to the amplification target region. The length of the base sequence of each probe is 21 to 31 mer.

In FIG. 8A, the plot at position 50 (horizontal axis) indicates the fluorescence intensity due to the antisense-strand probe, and each plot at positions 65 to 120 (horizontal axis) indicates the fluorescence intensity due to the sense-strand probe.

As shown in FIG. 8A, the fluorescence intensity increased as the position of the probe was closer to the 3'-end of the amplification target region when using the sense-strand probe. In particular, the fluorescence intensity was high when the position of the probe was within the 3'-end half of the amplification target region.

A fluorescence intensity higher than that of the sense-strand probe (position 65) was obtained by the antisense-strand probe (position 50). The antisense-strand probe is further described below in connection with Experiment 4 (FIG. 8C).

Experiment 3

A plurality of probes that respectively hybridize to various positions of an invasion gene (amplification target region) of *Salmonella* were prepared. The genomic DNA of *Salmonella* was amplified using the primer set having the base sequences of SEQ ID NO: 60 and 61. Each probe was hybridized to the resulting amplified product, and the fluorescence intensity was measured in the same manner as in Example 1. The results are shown in FIG. 8B.

In FIG. 8B, each plot indicates the fluorescence intensity due to the sense-strand probe. As shown in FIG. 8B, the fluorescence intensity increased as the position of the probe was closer to the 3'-end of the amplification target region when using the sense-strand probe. In particular, the fluorescence intensity was high when the position of the probe was within the 3'-end half of the amplification target region.

The fluorescence intensity due to the probe at position 118 (horizontal axis) was lower to some extent than the fluorescence intensity due to the probe at position 112 (horizontal axis). It is conjectured that the decrease in fluorescence intensity occurred due to saturation.

Experiment 4

A plurality of probes that respectively hybridize to various positions of a ribosomal gene (amplification target region) of Campylobacter were prepared. The genomic DNA of Campylobacter was amplified using the primer set having the base sequences of SEQ ID NO: 54 and 55. Each probe was hybridized to the resulting amplified product, and the fluorescence intensity was measured in the same manner as in Example 1. The results are shown in FIG. 8C.

In FIG. 8C, each plot indicates the fluorescence intensity due to the antisense-strand probe. As shown in FIG. 8C, the fluorescence intensity increased as the position of the probe was closer to the 5'-end of the amplification target region when using the antisense-strand probe. In particular, the fluorescence intensity was high when the position of the probe was within the 5'-end half of the amplification target region.

It was confirmed by the results of Experiments 2 to 4 that the position of the probe in the PCR amplification target region and the fluorescence intensity have the following relationship.

Specifically, the fluorescence intensity increases as the position of the probe is closer to the 3'-end of the amplification target region, and decreases as the position of the probe is closer to the 5'-end of the amplification target region when using the sense-strand probe.

In contrast, the fluorescence intensity increases as the position of the probe is closer to the 5'-end of the amplification target region, and decreases as the position of the probe is closer to the 3'-end of the amplification target region when using the antisense-strand probe.

Example 2

Experiments were performed in order to check whether or not the carrier for detecting food poisoning bacteria according to the embodiment of the invention can simultaneously detect the seven types of detection target food poisoning bacteria.

A PCR reaction mixture having the following composition was used. The primers were synthesized by Life Technologies Japan Ltd. The other components are products manufactured by Takara Bio Inc.

Buffer solution "10×Ex Taq buffer" (20 mM Mg 2+ plus): 2.0 μl
Nucleic acid substrate "dNTP Mixture" (2.5 mM dATP, 2.5 mM dCTP, 2.5 mM dGTP, and 2.5 mM dTTP): 1.6 μl
primerF (10 ng/μl, final conc.: 2 ng): 0.2 μl×7
primerR (10 ng/μl, final conc.: 2 ng): 0.2 μl×7
PrimerF for detecting Vibrio: 0.4 μl
PrimerR for detecting Vibrio: 0.4 μl
Nucleic acid polymerase "EX Taq" (5 U/μl): 0.1 μl
Labeling component "Cy5": 0.2 μl
DNA sample: 1.0 μl×7
Sterilized water: 5.5 μl
(Total amount: 20 μl)

All of the primer sets shown in FIG. 3 that amplify the eight regions of the seven types of bacteria were used as the PCR primer sets. The following DNA samples were used in the same manner as in Experiment 1. All of the DNA samples were added to the PCR reaction mixture.
Strain 1: *Bacillus cereus* TIFT 114011
Strain 2: *Campylobacter jejuni* ATCC 33560
Strain 3: *Escherichia coli* NBRC 102203
Strain 4: *Listeria monocytogenes* ATCC 15313
Strain 5: *Salmonella enterica* ATCC 9270
Strain 6: *Staphylococcus aureus* NBRC 100910
Strain 7: *Vibrio parahaemolyticus* RIMD 2210050

The target region of the respective food poisoning bacteria was simultaneously amplified by PCR under the following conditions using a system "Mastercycler ep gradient" (manufactured by Eppendorf).
(1) 95° C./2 min
(2) 95° C./10 sec (DNA strand separation step (denaturation step))
(3) 68° C./30 sec (annealing step)
(4) 72° C./30 sec (DNA extension step)
(5) 72° C./2 min
The steps (2) to (4) were repeated in 40 cycles.

Figure 9:
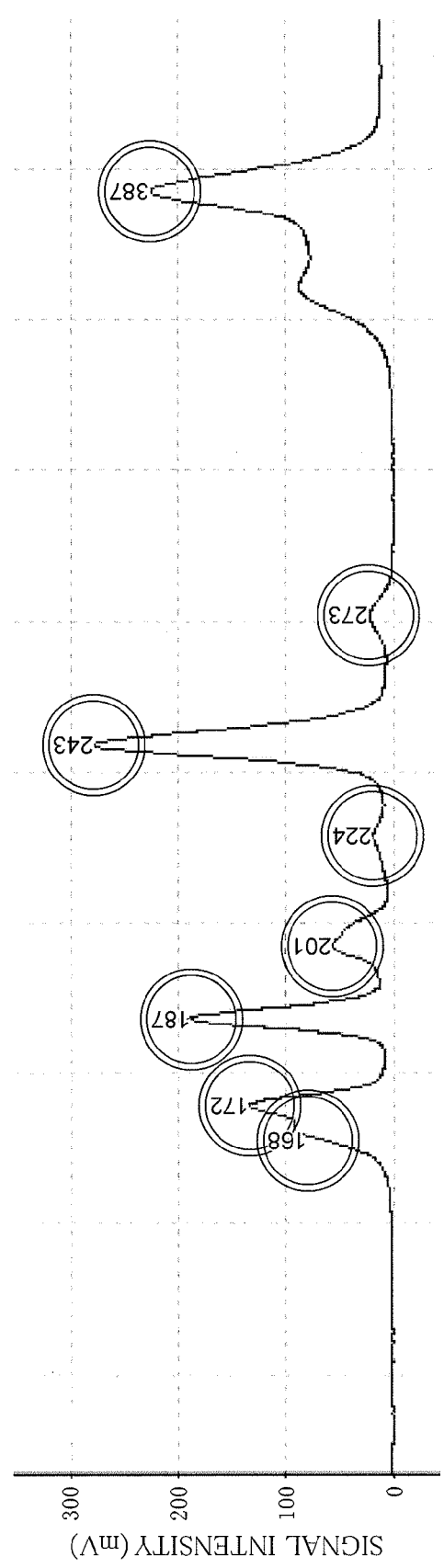
FIG. 9 is a view showing the multiplex PCR amplification results for the DNA of the target food poisoning bacteria using a method for detecting food poisoning bacteria according to one embodiment of the invention.

The PCR amplified product was subjected to electrophoresis to check whether or not a correct amplified product was obtained. Electrophoresis was performed using an electrophoresis system "MultiNA" (manufactured by Shimadzu Corporation). The results are shown in FIG. 9. As shown in FIG. 9, the following eight peaks were observed as a result of electrophoresis.
(1) 168 bp, (2) 172 bp, (3) 187 bp, (4) 201 bp, (5) 224 bp, (6) 243 bp, (7) 273 bp, (8) 387 bp It is considered that these peaks can be respectively attributed to the amplified products of the following strains taking account of the results obtained in Experiment 1.
(1) Strain 3 (*Escherichia coli* NBRC 102203)
(2) Strain 5 (*Salmonella enterica* ATCC 9270)
(3) Strain 4 (*Listeria monocytogenes* ATCC 15313)
(4) Strain 1 (*Bacillus cereus* TIFT 114011)
(5) Strain 6 (*Staphylococcus aureus* NBRC 100910)
(6) Strain 1 (*Bacillus cereus* TIFT 114011)
(7) Strain 2 (*Campylobacter jejuni* ATCC 33560)
(8) Strain 7 (*Vibrio parahaemolyticus* RIMD 2210050)

Therefore, it is considered that the PCR amplified product contained all of the amplified products of the eight regions of the seven types of food poisoning bacteria respectively obtained by the primer sets shown in FIG. 3.

Figure 10:
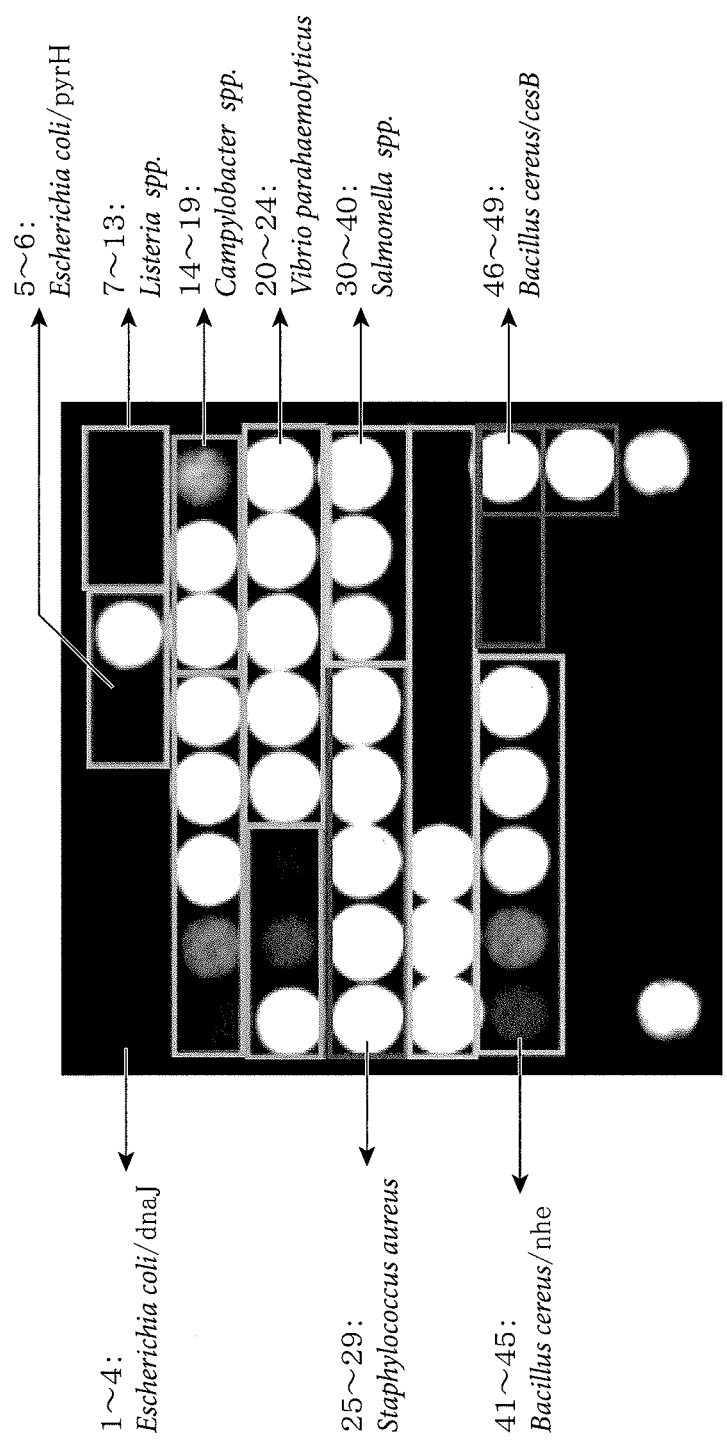
FIG. 10 is a view showing the simultaneous detection results (fluorescence photographs) obtained using a carrier for detecting food poisoning bacteria according to one embodiment of the invention.

The PCR amplified product was added dropwise to the carrier for detecting food poisoning bacteria according to the embodiment of the invention, and the label of the PCR amplified product that had hybridized to the probe immobilized on the carrier was detected in the same manner as in Example 1. FIG. 10 shows the results obtained by capturing (photographing) the detected fluorescence, and FIG. 11 shows the fluorescence intensity values.

As shown in FIG. 10, fluorescence was clearly detected for *Escherichia coli* from the spot 6. Fluorescence was clearly detected for *Listeria* from the spots 9 to 13. Fluorescence was clearly detected for *Campylobacter* from the spots 14 to 19. Fluorescence was clearly detected for *Vibrio parahaemolyticus* from the spots 20 to 24. Fluorescence was clearly detected for *Staphylococcus aureus* from the spots 25 to 29. Fluorescence was clearly detected for *Salmonella* from the spots 30 to 35. Fluorescence was clearly detected for *Bacillus cereus* from the spots 41 to 45, 48, and 49.

As shown in FIG. 11, fluorescence was detected for all of the probes respectively having a base sequence among the base sequences of SEQ ID NO: 5 to 49.

FIG. 12 summarizes the results obtained in Examples 1 and 2. As shown in FIG. 12, it was confirmed that the carrier for detecting food poisoning bacteria according to the embodiment of the invention could individually detect *Escherichia coli*, *Listeria*, *Campylobacter*, *Vibrio parahaemolyticus*, *Staphylococcus aureus*, *Salmonella*, and *Bacillus cereus*. It was also confirmed that the amplified products could be simultaneously amplified even when the PCR amplified product contained the amplified products of the eight regions of the seven types of food poisoning bacteria.

It was confirmed by the above results that the PCR amplified products of the eight regions of the seven types of food poisoning bacteria can be simultaneously detected using the carrier and the method for detecting food poisoning bacteria according to the embodiments of the invention.

Example 3

Experiments were performed in order to check whether or not a false-positive reaction occurs when using the probe immobilized on the carrier for detecting food poisoning bacteria according to the embodiment of the invention.

The experiments were performed in the same manner as in Example 2, except that the genomic DNA of one type of food poisoning bacteria was excluded from the PCR reaction mixture (i.e., the PCR reaction mixture contained the genomic DNA of six types of food poisoning bacteria).

Figure 13:
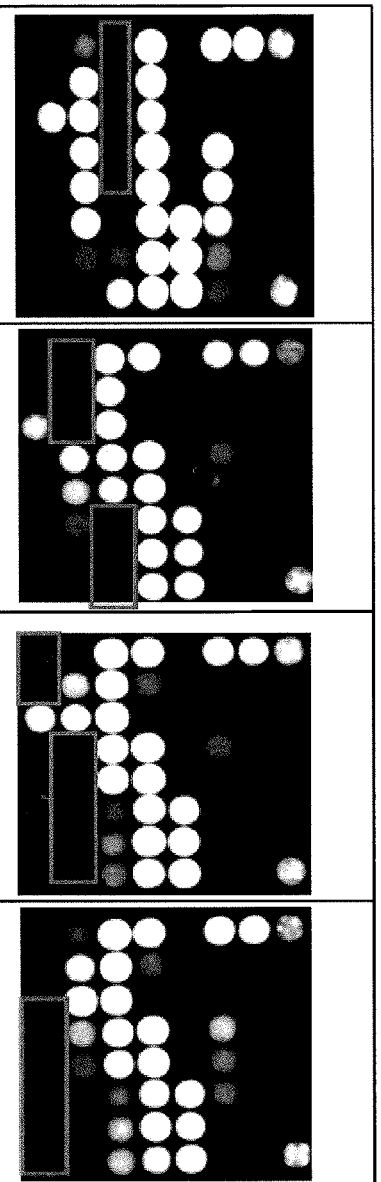
FIG. 13 is a view showing detection results 1 (results and fluorescence photographs) (i.e., the presence or absence of a false-positive reaction) obtained using a carrier for detecting food poisoning bacteria according to one embodiment of the invention.
Figure 14:
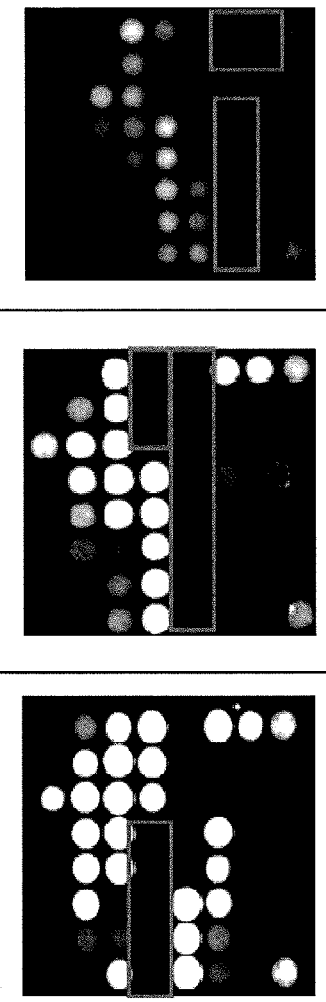
FIG. 14 is a view showing detection results 2 (results and fluorescence photographs) (i.e., the verification of a false-positive reaction) obtained using a carrier for detecting food poisoning bacteria according to one embodiment of the invention.

Whether or not fluorescence was detected from the spot on which the probe for the one type of food poisoning bacteria of which the genomic DNA was not contained in the PCR reaction mixture was immobilized, was determined. FIGS. 13 and 14 show the resulting fluorescence photographs, and FIGS. 15 and 16 show the fluorescence intensity values.

In FIGS. 13 and 14, numerals 1 to 7 indicate the number of each experiment that was performed independently. The food poisoning bacteria of which the genomic DNA was contained in the PCR reaction mixture are indicated by a circle, and the food poisoning bacteria of which the genomic DNA was not contained in the PCR reaction mixture are indicated by a cross. The item "Chip results" shows the fluorescence photograph in which the spots corresponding to the food poisoning bacteria of which the genomic DNA was not contained in the PCR reaction mixture are enclosed by a square. A case where fluorescence was not detected from the spots corresponding to the food poisoning bacteria of which the genomic DNA was not contained in the PCR reaction mixture is indicated by a circle (see "Probe specificity").

As shown in FIGS. 13 and 14, fluorescence was not detected from the spots corresponding to the food poisoning bacteria of which the genomic DNA was not contained in the PCR reaction mixture.

The fluorescence intensity values shown in FIGS. 15 and 16 also indicate that fluorescence was not detected from the spots corresponding to the food poisoning bacteria of which the genomic DNA was not contained in the PCR reaction mixture.

It was confirmed by the above results that the probes used for the carrier and the method for detecting food poisoning bacteria according to the embodiments of the invention exhibit excellent specificity, and can specifically and simultaneously detect the seven types of detection target food poisoning bacteria.

The invention is not limited to the above embodiments and examples. Various modifications may be made without departing from the scope of the invention.

For example, the components of the PCR reaction mixture may be appropriately changed as long as the PCR reaction mixture includes the PCR primer set and the sample, and similar effects can be obtained. The probe design method according to the embodiment of the invention may also be applied when designing probes for detecting the genomic DNA of other bacteria.

INDUSTRIAL APPLICABILITY

The invention may suitably be used when it is desired to simultaneously, specifically, and quickly determine (detect) whether or not *Escherichia coli*, *Listeria*, *Campylobacter*, *Vibrio parahaemolyticus*, *Staphylococcus aureus*, *Salmonella*, and/or *Bacillus cereus* are present in food, facilities (equipmen), and the like.

SEQUENCE LISTING

TSK1121 PCTSequenceFile

The invention claimed is:

1. A microarray for detecting food poisoning bacteria, the microarray comprising:
    a plurality of probes immobilized on the microarray, wherein the plurality of probes comprises: a probe from a first probe group, a probe from a second probe group, a probe from a third probe group, a probe from a fourth probe group, a probe from a fifth probe group, a probe from a sixth probe group, and a probe from a seventh probe group, wherein
    the probe from the first probe group hybridizes to a nucleic acid fragment of *Escherichia coli*, and the first probe group consists of probes consisting of SEQ ID NO: 1 to 4 or the complements thereof,
    the probe from the second probe group hybridizes to a nucleic acid fragment of *Listeria*, and the second probe group consists of probes consisting of SEQ ID NO: 7 to 13 or the complements thereof,
    the probe from the third probe group hybridizes to a nucleic acid fragment of *Campylobacter*, and the third probe group consists of probes consisting of SEQ ID NO: 14 to 19 or the complements thereof,
    the probe from the fourth probe group hybridizes to a nucleic acid fragment of *Vibrio parahaemolyticus*, and the fourth probe group consists of probes consisting of SEQ ID NO: 20 to 24 or the complements thereof,
    the probe from the fifth probe group hybridizes to a nucleic acid fragment of *Staphylococcus aureus*, and the fifth probe group consists of probes consisting of SEQ ID NO: 25 to 29 or the complements thereof,
    the probe from the sixth probe group hybridizes to a nucleic acid fragment of *Salmonella*, and the sixth probe group consists of probes consisting of SEQ ID NO: 30 to 40 or the complements thereof, and
    the probe from the seventh probe group hybridizes to a nucleic acid fragment of *Bacillus cereus*, and the seventh probe group consists of probes consisting of SEQ ID NO: 41 to 45 or the complements thereof,
        wherein the plurality of probes specifically and simultaneously hybridize to the nucleic acid fragments of *Escherichia coli, Listeria, Campylobacter, Vibrio parahaemolyticus, Staphylococcus aureus, Salmonella*, and *Bacillus cereus*.

2. The microarray of claim 1, wherein the plurality of probes comprises two probes selected respectively from each of all groups.

* * * * *